(12) United States Patent
Goodlett et al.

(10) Patent No.: US 6,629,040 B1
(45) Date of Patent: Sep. 30, 2003

(54) ISOTOPE DISTRIBUTION ENCODED TAGS FOR PROTEIN IDENTIFICATION

(75) Inventors: David R. Goodlett, Seattle, WA (US); James E. Bruce, Kennewick, WA (US); Beate Rist, Seattle, WA (US); Richard D. Smith, Richland, WA (US); Ruedi Aebersold, Mercer Island, WA (US)

(73) Assignees: University of Washington, Seattle, WA (US); Battelle Memorial Institute, Richland, WA (US)

(*) Notice: Subject to any disclaimer, the term of this patent is extended or adjusted under 35 U.S.C. 154(b) by 0 days.

(21) Appl. No.: 09/528,603

(22) Filed: Mar. 20, 2000

Related U.S. Application Data

(60) Provisional application No. 60/125,323, filed on Mar. 19, 1999.

(51) Int. Cl.$^7$ .......... G01N 31/00; G01N 19/00; G01N 33/48; B01D 59/44; A61K 38/00; C07K 14/00; C07K 1/00; C07K 17/00

(52) U.S. Cl. .......... 702/23; 702/19; 250/281; 530/300.35

(58) Field of Search ...... 702/19, 23; 250/281; 530/300.35

(56) References Cited

U.S. PATENT DOCUMENTS

| | | |
|---|---|---|
| 4,798,795 A | 1/1989 | Sigler .......... 435/177 |
| 5,240,859 A | 8/1993 | Aebersold .......... 436/89 |
| 5,438,017 A | 8/1995 | Allen et al. .......... 436/89 |
| 5,514,559 A | 5/1996 | Marker-Hahn et al. .... 435/7.92 |
| 5,527,711 A | 6/1996 | Tom-Moy et al. .......... 436/518 |
| 5,534,132 A | 7/1996 | Vreeke et al. .......... 205/777.5 |
| 5,534,440 A | 7/1996 | Aebersold et al. .......... 436/89 |
| 5,538,897 A | 7/1996 | Yates, III et al. .......... 436/89 |
| 5,614,368 A | 3/1997 | Ghazarossian et al. .......... 435/7.5 |
| 5,650,270 A | 7/1997 | Giese et al. .......... 435/6 |
| 5,658,725 A | 8/1997 | Schlieper et al. .......... 435/5 |
| 5,686,310 A | 11/1997 | Haystead et al. .......... 436/86 |
| 5,738,984 A | 4/1998 | Shoseyov .......... 435/4 |
| 5,851,781 A | 12/1998 | Adamczyk et al. .......... 435/7.9 |
| 5,863,740 A | 1/1999 | Kientsch-Engel et al. ... 435/7.5 |
| 5,880,270 A | 3/1999 | Berninger et al. .......... 530/391.1 |
| 5,952,653 A | 9/1999 | Covey et al. .......... 250/288 |
| 5,958,703 A | 9/1999 | Dower et al. .......... 435/7.1 |
| 5,965,131 A | 10/1999 | Griffiths et al. .......... 424/133.1 |
| 5,965,457 A | 10/1999 | Magnani .......... 436/518 |
| 6,017,693 A | 1/2000 | Yates, III et al. .......... 435/5 |
| 6,057,096 A | 5/2000 | Rothschild et al. .......... 435/6 |

FOREIGN PATENT DOCUMENTS

| | | | | |
|---|---|---|---|---|
| WO | WO 90/04786 | 5/1990 | .......... | G01N/33/53 |
| WO | WO98/26095 | 6/1998 | | |
| WO | WO 00/11208 | 2/2000 | .......... | C12Q/1/00 |
| WO | WO00/11208 | 3/2000 | | |
| WO | WO 01/96869 A1 | 12/2001 | .......... | G01N/33/53 |

OTHER PUBLICATIONS

Rawn J. D., Biochemistry, 1989, Neil Patterson Publishers, pp. 68–69.*

Yip et al., Tech. Protein Chem. IV, [Pap. Protein Soc. Symp.], 6th, 1993. See Abstract.*

Ogryzko et al., Cell, 1998, vol. 94, pp. 35–44.*

Girault, S., "Coupling of Maldi–Tof Mass Analysis to the Separation of Biotinylated Peptides by Magnetic Streptavidin Beads"; (1996) *Anal. Chem.* 68:2122–2126.

Nelson, R., "The Use of Bioreactive Probes in Protein Characterization"; (1997) *Mass Spectrometry Reviews* 16:353–376.

Schriemer, D. and Li, L., "Combining Avidin–Biotin Chemistry with Matrix–Assisted Laser Desorption/Ionization Mass Spectrometry"; (1996) *Anal. Chem.* 68:3382–3387.

Schriemer, D. et al., "Maldi Mass Spectrometry Combined with Avidin–Biotin Chemistry for Analysis of Protein Modifications"; (1998) *Anal. Chem.* 70:1569–1575.

Whittal, R. et al., "Nanoliter Chemistry Combined with Mass Spectrometry for Peptide Mapping of Proteins from Single Mammalian Cell Lysates"; (1998) *Anal. Chem.* 70: 5344–5347.

Yates, John R., "Mass Spectrometry and the Age of the Proteome"; (1998) *Journal of Mass Spectrometry* 33:1–19.

Aebersold, R. et al. "Determination of the site of tyrosine phosphorylation at the low picomole level by automated solid–phase sequence analysis" (1991) Anal. Biochem. 199:51–60.

Boucherie, H. et al., "Two–dimensional gel protein database of *Saccharomyces cerevisiae*" (1996) Electrophoresis 17:1683–1699.

Bruce, J. E. et al., "Obtaining More Accurate FTICR Mass Measurements Without Internal Standards using Multiply Charged Ions," (Jan. 2000) J. Am. Soc. Mass Spec. 11(5):416–421.

Futcher, B. et al., "A Sampling of the Yeast Proteome" (Nov. 1999) Mol. Cell. Bio. 19(11):7357–7368.

Gingras, A.C. et al., "Regulation of 4E–BP1phosphorylation: a novel two–step mechanism" (Jun. 1999) Genes Dev. 13:1422–1437.

(List continued on next page.)

*Primary Examiner*—John S. Brusca
*Assistant Examiner*—Shubo Zhou
(74) *Attorney, Agent, or Firm*—Greenlee, Winner and Sullivan, P.C.

(57) ABSTRACT

The present invention provides methods and reagents for identifying specific masses of compounds in a complex mixture. In particular, the present invention describes an isotope distribution encoded tag (IDEnT) concept wherein the ability to distinguish an analyte encoded with a non-native isotope from those not encoded with the isotope or from those encoded with a different isotope is used for protein identification, enzyme active site identification, peptide sequencing, and the like. Reagents used in the IDEnT strategy consist of a chemical element with a unique isotope distribution not normally found in the analyte class being studied, chemically bonded to, or an integral part of a chemical reagent with a high selectivity of affinity for specific functional group in the analyte.

47 Claims, 6 Drawing Sheets

OTHER PUBLICATIONS

Goodlett, D.R. et al., "Protein identification with a single accurate mass of a cystein–containing peptide and constrained database searching" (Mar. 2000) Anal. Chem. 72(6):1112–1118.

Goodlett, D.R. et al., "Quantitative in Vitro kinase reaction as a guide for phosphoprotein analysis by mass spectrometry" (Mar. 2000) Rapid Commun Mass Spectrom. 14(5):344–348.

Graves, J.D. & Krebs, ED. "Protein phosphorylation and signal transduction" (May 1999) Pharmacol. Ther. 82(2–3):111–121.

Haynes, P.A. et al., "Proteome Analysis: Biological Assay or Data Archive?" (1998) Electrophoresis vol. 19:1862–1871.

Hunter, T. "1001 protein kinases redux—towards 2000" (1994) Semin. Cell Biol. 5:367–376.

Jonscher, K.R. and Yates, J.R. III, "Matrix–assisted laser desorption ionization/quadrupole ion trap mass spectrometry of peptides. Application to the localization of phosphorylation sites on the P protein from Sendai virus"(Jan. 1997) J,. Biol. Chem. 272(3):1735–1741.

Koch, C.A. et al., "SH2 and SH3 domains: elements that control interactions of cytoplasmic signaling proteins" (1991) Science 252:668–674.

McCormack, A.L. et al. "Direct Analysis and Identification of Proteins in Mixtures by LC/MS/MS and Database Searching at the Low–Femtomole Level" (1997) Anal. Chem. 69:767–776.

Papayannopoulos, I.A., "The interpretation of collision–induced dissociation tandem mass spectra of peptides" (1995) Mass Spectrometry Rev. 14:49–73.

Qin, J. and Chait, B.T., "Identification and characterization of posttranslational modifications of proteins by MALDI ion trap mass spectrometry" (1997) Anal. Chem. 69 (19):4002–4009.

Verma, R. et al. "Phosphorylation of Sic1p by $G_1$ Cdk required for its degradation and entry into S Phase" (1997) Science 278(5337):455–460.

Watts, J.D. et al., "Identification by electrospray ionization mass spectrometry of the sites of tyrosine phosphorylation induced in activated Jurkat T cells on the protein tyrosine kinase ZAP–70" (1994) J. Biol. Chem. 269(47):29520–29529.

Duncan, M.W., and Poljak, A., "Amino Acid Analysis of Peptides and Proteins on the Femptomole Scale by Gas Chromatography/Mass Spectrometry" (1998) Anal. Chem. 70:890–896.

Figeys, D. et al., "A Microfabricated Device for Rapid Protein Identification by Microelectrospray Ion Trap Mass Spectrometry" (1997) Anal. Chem. 69:3153–3160.

Gygi, S. P. et al., "Quantitative analysis of complex protein mixtures using isotope–coded affinity tags" (Oct. 1999) Nature Biotechnology 17:994–999.

Qin, J. et al., "De Novo Peptide Sequencing in an Ion Trap Mass Spectrometer with $^{18}O$ Labeling" (1998) Rapid Communications in Mass Spectrometry 12:209–216.

Ashikaga, K. et al. (1988), "Intramolecular End–to–End Reactions of Photoactive Terminal Groups Linked by Poly-(oxyethylene) Chains," Bull. Chem. Soc. Jpn. 61:2443–2450.

Bayer, E. and Wilchek, M. (1990), "Biotin–Binding Proteins: Overview and Prospects," Methods Enzymol. 184:49–51.

Brockhausen, I. et al. (Jul. 1989), "Control of glycoprotein synthesis," J. Biol. Chem. 264:11211–11221.

Chapman, A. et al. (May 1980), "The primary glycosylation defect in class B Thy–1 negative mutant mouse lymphoma cells is an inability to synthesize dolichol–P–mannose," J. Biol. Chem. 255:4441–4446.

Clauser, K.R. et al. (1995), "Rapid mass spectrometric peptide sequencing and mass matching for characterization of human melanoma proteins isolated by two–dimensional page," Proc. Natl. Acad. Sci. USA 92:5072–5076.

De Leenheer, A.P. and Thienpont, L.M. (1992), "Applications of isotope dilution–mass spectrometry in clinical chemistry, pharmacokinetics, and toxicology," Mass Spectrom. Rev. 11:249–307.

DeRisi, J.L. et al. (Oct. 1997), "Exploring the metabolic and genetic control of gene expression on a genomic scale," Science 278:680–6.

Dongré, A. R. et al. (Oct. 1997), "Emerging tandem- –mass–spectrometry techniques for the rapid identification of proteins," Trends Biotechnol. 15:418–425.

Ducret et al. (1998), "High througput protein characterization by automated reverse–phase chromatography/electrospray tandem mass spectrometry," Protein Sci. 7:706–719.

Eng et al. (1994), "An approach to Correlate Tandem Mass Spectral Data of Peptides with Amino Acid Sequences in a Protein Database," J. Am. Soc. Mass Spectrom. 5:976–989.

Figeys, D. et al. (1998), "Electrophoresis combined with novel mass spectrometry techniques: Powerful tools for the analysis of proteins and proteomes," Electrophoresis 19:1811–1818.

Figeys, D. and Aebersold, R. (1998), "High sensitivity analysis of proteins and peptides by capillary electrophoresis tandem mass spectrometry: Recent developments in technology and applications," Electrophoresis 19:885–892.

Figeys, D. et al. (Nov. 1996), "Protein identification by solid phase microextraction–capillary zone electrophoresis–microelectrospray–tandem mass spectrometry," Nature Biotech. 14:1579–1583.

Figeys, D. et al. (1997), "A microfabricated device for rapid protein identification by microelectrospray ion trap mass spectrometry," Anal. Chem. 69:3153–3160.

Freeze, H. H. (Nov. 1998), "Disorders in protein glycosylation and potential therapy," J. Pediatrics 133:593–600.

Freeze, H. H. (1999), "Human glycosylation and disorders sugar supplement therapy," Biochem. Biophys. Res. Commun. 255:189–193.

Gamper, H.B. (1993), "Facile Preparation of Nuclease Resistant 3 ' Modified Oligodeoxynucleotides," Nucl. Acids Res. 21:145–150.

Garrels, J. I. et al. (1997), "Proteome studies of Saccharomyces cerevisiae: identification and characterization of abundant proteins," Electrophoresis, 18:1347–1360.

Gerber, S.A. et al. (1999), "Analysis of rates of multiple enzymes in cell lysates by electrospray ionization mass spectrometry," J. Am. Chem. Soc. 121:1102–1103.

Glaser, L. (1966) Phosphomannomutase from yeast. In Meth. Enzymol. vol. VIII, Neufeld, E. F.; Ginsburg, V. Eds; Academic Press: New York 1966, pp. 183–185.

Gygi et al. (Mar. 1999), Correlation between Protein and mRNA Abundance in Yeast, Mol. Cell. Bio. 19(3):1720–1730.

Gygi et al. (1999), "Protein analysis by mass spectrometry and sequence database searching: tools for cancer research in the post–genomic era," *Electrophoresis* 20:310–319.

Haynes, P. A. et al. (1998), "Identification of gel–separated proteins by liquid chromatography electrospray tandem mass spectrometry: Comparison of methods and their limitations," *Electrophoresis* 19:939–945.

Hodges et al. (1999), "The Yeast Proteome Database (YPD): a model for the organization and presentation of genome–wide functional data," *Nucleic Acids Res.* 27(1):69–73.

Kataky, R. et al. (1990), "Comparative Study of Mono– and Di–substituted 14–Crown–4 Derivatives as Lithium Ionophores," *J. Chem. Soc. Perkin Trans.* 2(2):321–327.

Kaur, K. J. and Alton, G.; Hindsgaul, O. (1991), "Use of N–acetylglucosaminyl–transerases I and II in the preparative synthesis of oligosaccharides," *Carbohydr. Res.* 210:145–153.

Kaur, K. J. and Hingsgaul, O. (1991) "A simple synthesis of octyl 3,6–O–($\alpha$–D–mannopyranosyl)–$\beta$–D–manopyranoside and its use as an acceptor for the assay of N–acetyglucosaminetransferase I activity," *Glycoconjugate J.* 8:90–94.

Körner, C. et al. (Oct. 1998), "Carbohydrate–deficient glycoprotein syndrome type V: deficiency of dolichyl–P–Glc:Man$_9$GlcNAc$_2$–PP–dolichyl glucosyltransferase," *Proc. Natl. Acad. Sci. U.S.A.* 95:3200–13205.

Link, A. J. et al. (1997), "Identifying the major proteome components of Haemophilus influenzae type–strain NCTC 8143," *Electrophoresis* 18:1314–1334.

Link, J. et al. (Jul. 1999), "Direct analysis of large protein complexes using mass spectrometry," *Nat. Biotech.* In press.

Mann, M. and Wilm, M. (Dec. 1994), "Error–Tolerant Identification of Peptides in Sequence Databases by Peptide Sequence Tags," *Anal. Chem.* 66:4390–4399.

McMurry, J. E. and Kocovsky, P. (1984), "A method for the palladium–catalyzed allylic oxidation of olefins," *Tetrahedron Lett.* 25, 4187–4190.

Morris, A.A.M. and Turnbull, D.M. (1994), "Metabolic disorders in children," *Curr. Opin. Neurol.* 7:535–541.

Oda, Y. et al. (Jun. 1999), "Accurate quantitation of protein expression and site–specific phosphorylation," *Proc. Natl. Acad. Sci. USA* 96:6591–6596.

Okada, S. and O'Brien, J.S. (May 1968), "Generalized Gangliosides: Beta–Galactosidase Deficiency," *Science* 160:1002–1004.

Opiteck, G.J. et al. (Apr. 1997), "Comprehensive on–line LC/LC/MS of proteins," *Anal. Chem.* 69:1518–1524.

Paulsen, H. and Meinjohanns, E. (Aug. 1992), "Synthesis of modified oligosaccharides of N–glycoproteins intended for substrate specificity studies of N–acetylglucosaminyltransferases II–V," *Tetrahedron Lett.* 33:7327–7330.

Paulsen, H. et al. (1993) Synthese von modifizierten Oligosacchariden der N–Glycoprotein zur Untersuchung der Spezifitat der N–Acetylglucosaminyltransferase II, *Liebigs Ann. Chem.* pp. 721–735.

Pennington, S. R. et al. (Apr. 1997), "Proteome analysis: from protein characterization to biological function," *Trends Cell Bio.* 7:168–173.

Qin, J. et al. (Oct. 1997), "A strategy for rapid, high–confidence protein identification," *Anal. Chem.* 69:3995–4001.

Romanowska et al. (1994), "Serological and Structural Features of Hafnia Alvei Lipopolysaccharides containing D–3–hydroxybutyric Acid," *FEMS Immunol. Med. Microbiol.* 8(1):83–8.

Romanowska, A. (1994), "Michael Additions for Synthesis of Neoglycoproteins," *Methods Enzymol.* 242:90–101.

Ronin, C. et al. (1981), "Transfer of glucose in the biosynthesis of thyroid glycoproteins. I. Inhibition of glucose transfer to oligosaccharide lipids by GDP–mannose," *Biochim. Biophys. Acta* 674, 48–57.

Ronin, C. et al. (1981a), "Synthetic substrates for thyroid oligosaccharide transferase. Effects of peptide chain length and modifications in the –Asn–Xaa–Thr–region," *Eur. J. Biochem.* 118, 159–164.

Ronne, H. (Jan. 1995), "Glucose repression in fungi," *Trends Genet.* 11:12–17.

Roth, F.P. et al. (Oct. 1998), "Finding DNA regulatory motifs within unaligned noncoding sequences clustered by whole–genome mRNA quantitation," *Nat. Biotechnol.* 16:939–945.

Rush, J. S. and Wachter, C. J. (Aug. 1995), "Transmembrane movement of a water–soluble analogue of mannosylphosphoryldolichol is mediated by an endoplasmic reticulum protein," *J. Cell. Biol.* 130:529–536.

Rush and Wachter (1995), "Method for determination of cellular levels of guanosine–5'–diphosphate–mannose based on a weak interaction with concanavalin A at low pH," *Anal. Biochem.* 224(2):494–501.

Schachter, H. (1986), "Biosynthetic controls that determine the branching and microheterogeneity of protein–bound oligosaccharides," *Biochem. Cell Biol.* 64, 163–181.

Shalon, D. et al. (1996), "A DNA microarray system for analyzing complex DNA samples using two–color fluorescent probe hybridization," *Genome Res.* 6:639–645.

Shevchenko, A. et al. (Dec. 1996), "Linking genome and proteome by mass spectrometry: large–scale identification of yeast proteins from two dimensional gels," *Proc. Natl. Acad. Sci. U.S.A.* 93:14440–14445.

Shevchenko, A. et al. (Mar. 1996), "Mass Spectrometric Sequencing of Proteins from Silver–Stained Polyacrylamide Gels," 68:850–858.

Tan, J. et al. (1996), "Mutations in the MGAT2 gene controlling complex glycan synthesis cause carbohydrate deficient glycoprotein syndrome type II, an autosomal recessive disease with defective brain development," *Am. J. Hum. Genet.* 59:810–817.

Velculescu, V. E. et al. (Jan. 1997), "Characterization of the yeast transcriptome," *Cell* 88:243–251.

Wilbur et al. (1997), "Biotin Reagents for Antibody Pretargeting. 2. Synthesis and in Vitro Evaluation of Biotin Dimers and Trimers for Cross–Linking of Streptavidin," *Bioconjugate Chem.* 8(6):819–832.

Wilbur, D.S. et al. (1997), "Biotin Reagents for Antibody Pretargeting. Synthesis, Radioiodination, and in Vitro Evaluation of Water Soluble, Biotinidase Resistant Biotin Derivatives," *Bioconjugate Chem.* 8:572–584.

Yates, J. R. et al. (Apr. 1995), "Method to correlate tandem mass spectra of modified peptides to amino acid sequences in the protein database," *Anal. Chem.* 67:1426–1436.

Bennetzen, J.L. and Hall, B.D. (Mar. 1982), "Codon Selection in Yeast," *J. Biol. Chem.* 257(6):3026–3031.

Bruce et al. (2000), "Obtaining More Accurate FTICR Mass Measurements Without Internal Standards using Multiply Charged Ions," *J. Am. Soc. Mass Spec.* 11(5):416–421.

Bruce et al. (Jul. 1999), "High–Mass–Measurement Accuracy and 100% Sequence Coverage of Enzymatically Digested Bovine Serum Albumin from an ESI–FTICR Mass Spectrum," *Anal. Chem.* 71(14):2595–2599.

Davis et al. (1996), "Rapid Protein Identification Using a Microscale Electrospray LC/MS System on an Ion Trap Mass Spectrometer," *J. Am. Soc. Mass. Spec.* 9:194–201.

Ducret et al. (1998), "High throughput protein characterization by automated reverse–phase chromatography/electrospray tandem mass spectrometry," *Protein Sci.* 7:706–719.

Fraser et al. (Dec. 1997), "Genomic se *quence of a Lyme disease spirochaete, Borrelia burgdorferi,"* Nature 390:580–586.

Fenyo et al. (1998), "Protein indentification using mass spectrometric information," *Electrophoresis* 19:998–1005.

Goffeau et al. (Oct. 1996), "Life with 6000 Genes," *Science* 274:546–549.

Goodlett et al. (1993), "Reduced Elution Speed Detection for Capillary Electrophoresis/Mass Spectrometry," *J. Microcolumn Separations* 5:57–62.

Henzel, et al., (Jun. 1993), "Identifying proteins from two–dimensional gels by molecular mass searching of peptide fragments in protein sequence databases ," *Proc. Natl. Acad. Sci. USA* 90:5011–5015.

Horn, et al., (1998), "A Computer Program for Automated Analysis of High Resolution Mass Spectra," *Proceedings of the 46th ASMS Conf. on Mass Spectrometry and Allied Topics, Orlando, FL May 31–Jun. 4, 1998*, p. 118.

Laemmli, U.K. (Aug. 1970), "Cleavage of Structural Proteins during the Assembly of the Head of Bacteriophage T4," *Nature* 277:680–695.

Lee et al. (1998), "HLA–E Surface Expression Depends on Binding of TAP–Dependent Peptides Derived from Certain HLA Class I Signal Sequences," *J. Immunol.* 160:4951–4960.

Lundell, N. and Schreitmuller, T. (1999), "Sample Preparation for Peptide Mapping—A Pharmaceutical Quality–Control Perspective," *Anal. Biochem.*266:31–47.

Marshall et al. (1998), "Fourier Transform Ion Cyclotron Resonance Mass Spectrometry: A Primer," *Mass. Spectrom. Rev.* 17:1–35.

Mosely et al. (1991), "Nanoscale Packed–Capillary Liquid Chromatography Coupled with Mass Spectrometry Using a Coaxial Continuous–Flow Fast Atom Bombardment Interface," *Anal. Chem.* 63:1467–1473.

Neubauer et al. (Sep. 1998), "Mass spectrometry and EST––database searching allows characterization of the multi––protein spliceosome complex," *Nature Genetics* 20:46–50.

Patterson et al. (1995), "Mass spectrometric approaches for the identification of gel–separated proteins," *Electro.* 16:1791–1814.

Sechi, S. and Chait, B.T. (Dec. 1998), "Modification of Cysteine Residues by Alkylation. A Tool in Peptide Mapping and Protein Identification," Anal. *Chem.* 70(24):5150–5158.

Susin et al. (Feb. 1999), "Molecular Characterization of Mitochondrial apoptosis–inducing factor," *Nature* 397:441–446.

Winger et al. (1993), "High–Resolution Accurate Mass Measurements of Biomolecules Using a New Electrospray Ionization Ion Cyclotron Resonance Mass Spectrometer," *J. Am. Soc. Mass Spec.* 4:566–577.

* cited by examiner

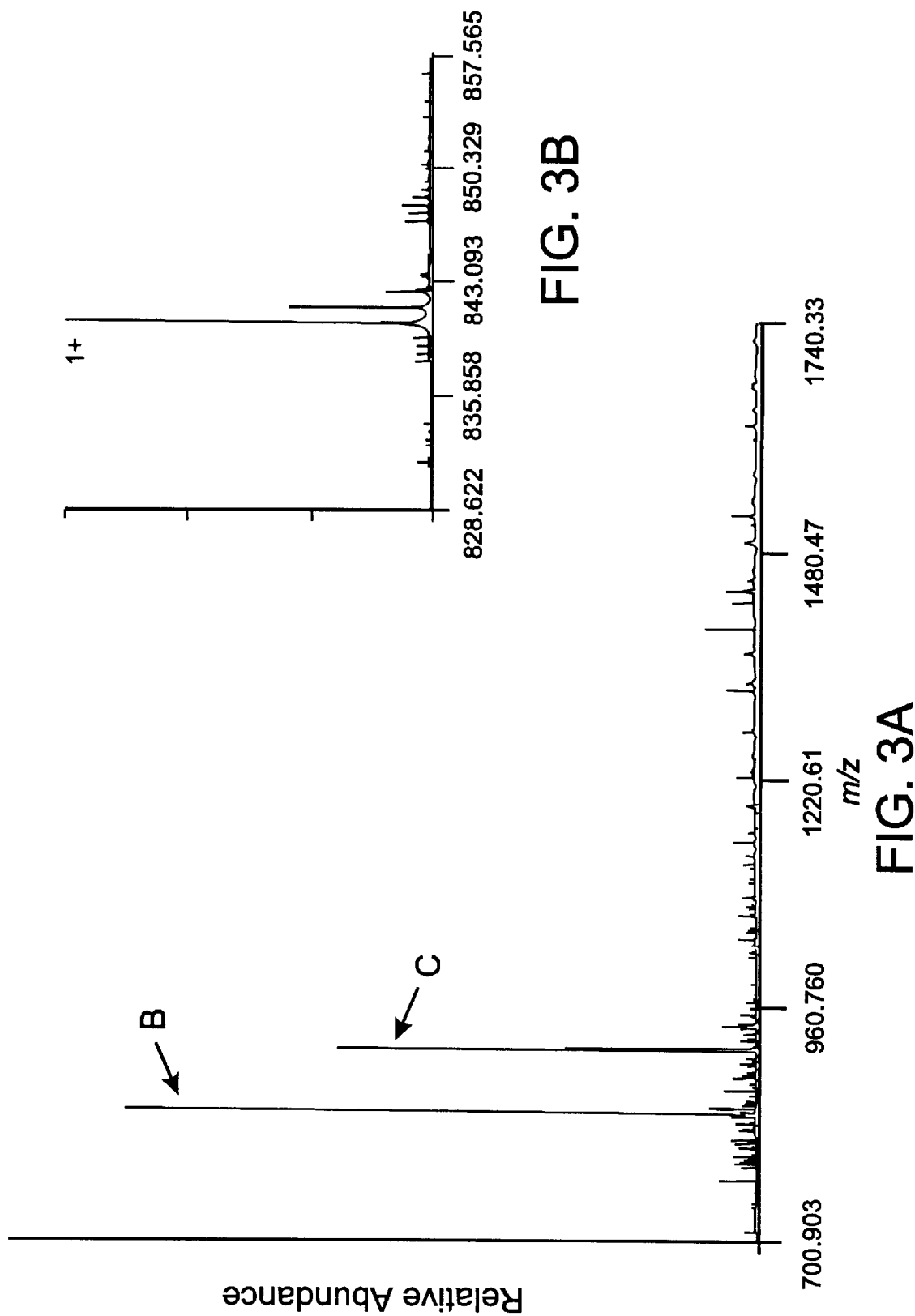

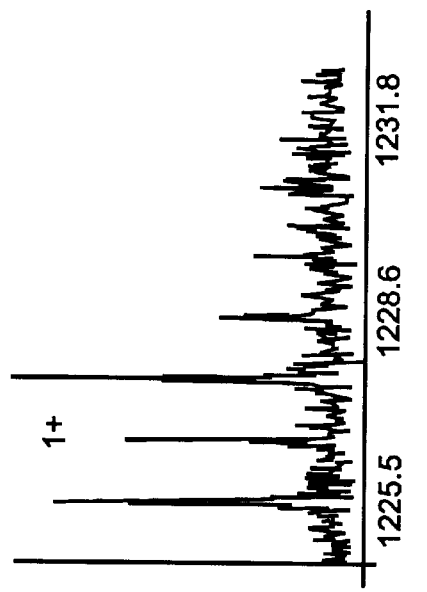
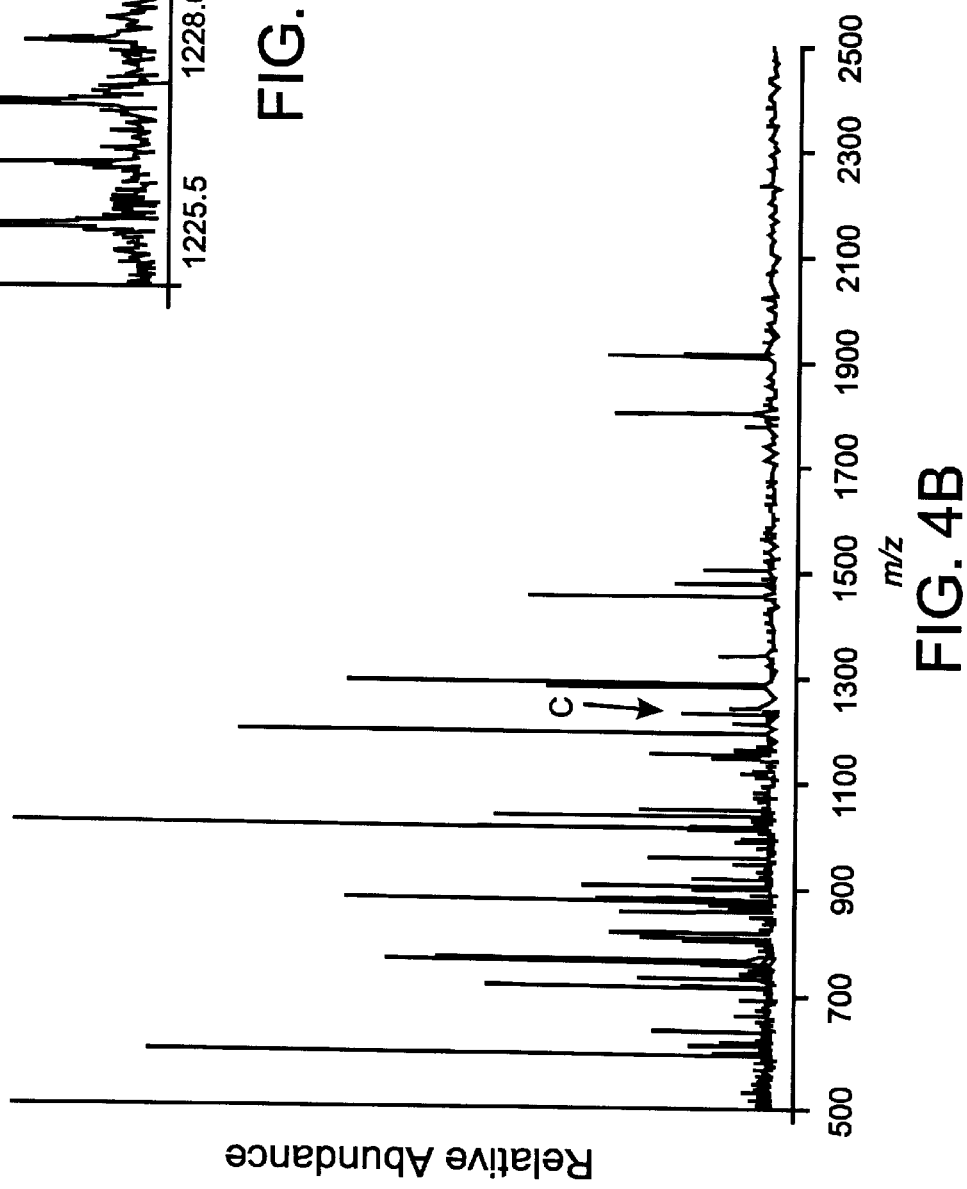
FIG. 4C
FIG. 4B

US 6,629,040 B1

ISOTOPE DISTRIBUTION ENCODED TAGS FOR PROTEIN IDENTIFICATION

CROSS-REFERENCE TO RELATED APPLICATIONS

This application claims the benefit of U.S. provisional patent application Ser. No. 60/125,323, filed Mar. 19, 1999, which is incorporated in its entirety by reference herein to the extent not inconsistent with the disclosure herewith.

STATEMENT REGARDING FEDERALLY SPONSORED RESEARCH OR DEVELOPMENT

This invention was developed under the National Science and Technology Center for Molecular Biotechnology. National Science Foundation (NSF) grant number BIR 9214-821 AM04. The U.S. government has certain rights in this invention.

BACKGROUND OF THE INVENTION

Traditionally, protein sequences were determined by stepwise, chemical degradation of purified proteins or fragments thereof. With the advent of sequence databases which contain complete genomic sequences or large numbers of complete or partial expressed gene sequences (expressed sequence tags, EST's) (Goffeau et al. (1996), Science 274:546–549; Fraser et al. (1977) Nature 390:580–586; Neubauer et al. (1998) Nature Genetics 20:46–50), the sequences of most proteins can be determined by correlating experimental data extracted from the protein with sequence databases (Henzel et al. (1993) Proc. Natl. Acad. Sci. USA 90:5011–5015; Eng et al. (1994) J. Am. Soc. Mass. Spectrom. 5:976–989). The many implemented sequence database searching strategies have in common the use of a combination of specific constraints to narrow down a candidate list of matching proteins in a database to a single protein (Patterson et al. (1995) Electrophoresis 16:1791–1814). Currently, the most restrictive constraints are generated by mass spectrometric (MS) or tandem mass spectrometric (MS/MS) analysis of peptide mixtures after proteolysis of a purified protein or protein mixture with a specific protease.

The constraints provided by collision-induced dissociation (CID) of selected peptides are highly discriminating because CID spectra reflect the amino acid sequence of the peptide analyzed. MS/MS is generally practiced with peptides separated by capillary HPLC or capillary electrophoresis (CE) connected on-line to an electrospray ionization (ESI) MS/MS instrument. Peptides eluting from the separation system are detected by the first stage mass analyzer that also selects peptide ions automatically for CID followed by fragment analysis in a second mass analyzer. Observed spectra are used to identify the protein from which the peptide originated, either by automated correlation of uninterpreted CID spectra with a sequence database or by searching sequence databases with complete or partial peptide sequences obtained by manual or computer-assisted interpretation of CID spectra (Eng et al. (1994) J. Am. Soc. Mass. Spectrom. 5:976–989; Mann et al. (1994) Anal. Chem. 66:4390–4399, each incorporated herein by reference). The method has the significant advantage that a CID spectrum from a single peptide is sufficient to conclusively identify a protein (Susin et al. (1999) Nature 397:441–446, incorporated herein by reference in its entirety). Consequently, proteins can be identified by correlating CID spectra with databases containing incomplete gene sequences as found in EST databases. Components of protein mixtures can be identified without the need for purification and proteins can be identified across species, provided that the peptide segment analyzed is conserved between species. The method has the disadvantage that peptide ions need to be sequentially selected for CID out of a mixture of analytes (Ducret et al. (1998) Protein Science 7:706–719). The number of peptides present in a mixture may significantly exceed the number of CID spectra generated in the time available for analysis. For automated MS/MS operation the mass spectrometer is generally programmed to give highest priority for CID selection to ions with the highest ion current (Ducret et al. supra). Therefore, if complex peptide mixtures are analyzed, lower intensity peptide ions will not be selected for CID. This results in an apparent compression of the dynamic range that can be somewhat alleviated, but not eliminated, by extending the peptide analysis time (Goodlett et al. (1993) J. Microcolumn Separations 5:57–62; Davis et al. (1996) J. Am. Soc. Mass. Spectrom. 9:194–201, each incorporated herein by reference in their entirety).

The accurately measured masses of peptides in a protein digest represent a different type of constraint for database searching. Such peptide mass profiles or fingerprints are determined in a single stage of mass spectrometry without CID. The list of observed peptide masses, together with auxiliary constraints including the estimated molecular weight of the unfragmented parent protein and the cleavage specificity of the protease used are then searched against sequence databases using any one of a number of available algorithms (Henzel et al. (1993) Proc. Natl. Acad. Sic. USA 90:5011–5015; Patterson et al. (1995) Electrophoresis 16:1791–1814, each incorporated herein). Peptide mass mapping identifies proteins without sequence specific information because the subset of peptide masses created by digestion of a protein with a specific protease defines the N- or C-terminal boundary of each fragment and thus provides a set of constraints unique to a given protein. The more accurately peptide masses are measured and the more peptide masses are detected from the same protein, the more conclusively the protein identity can be determined (Fenyö et al. (1998) Electrophoresis 19:998–1005, incorporated herein by reference). The peptide mass mapping approach has the advantage over the MS/MS strategy that the mass spectrometer operates in full scan mode (i.e., in a single stage) for the duration of the experiment, and should generally provide greater sensitivity. However, the method generally fails to identify the components of protein mixtures because it cannot be determined from which parent protein a specific peptide or set of peptides originated. Peptide mass fingerprinting is also incompatible with searching EST databases because it is unlikely that a sufficient number of peptide masses will match a single EST to provide an unambiguous correlation.

The present invention describes a class of reagents designated Isotope Distribution Encoded Tags (IDEnTs) and a method using the IDEnT concept for protein identification by accurate mass measurement of a single peptide, combining the strengths of the CID and peptide mass mapping approaches. Recent calculations for proteins expressed by the genomes of *E. coli* and *S. cerevisiae*, indicate that at 0.1 ppm mass accuracy 96% of the proteins will generate tryptic peptides with a unique mass, suggesting the feasibility of protein identification based on the mass of a single peptide. Inclusion of additional constraints such as the estimated molecular weight of the parent protein, the cleavage specificity of the protease used to digest and parent protein and the presence of an uncommon amino acid such as cysteine, methionine or tryptophane in the peptide sequence further enhances the stringency of the database search. Among these constraints the presence of cysteine in a peptide sequence is particularly attractive because the sulfhydryl side chain of cysteine residues is chemically distinct among amino acid residues and its presence significantly constrains the database search while still covering 92% of the open reading frames in yeast (Sechi and Chait (1998) Anal. Chem. 70:5150–5158). To employ this cysteine constraint for protein identification, it is essential that the cysteine-containing peptides be recognized in a peptide mixture. To this end a cysteine-specific alkylating reagent was synthesized which allows mass spectrometric identification of cysteine-containing peptides by the covalent addition of an isotope-distribution encoded tag or IDEnT (Lundell and Schreitmuller (1999) Anal. Biochem. 266:31–47).

SUMMARY OF THE INVENTION

The present invention describes an analytical strategy and the basic chemical concepts necessary to identify proteins in a sequence database from the accurately measured mass/charge of a single peptide using high-resolution mass spectrometry and a sequence constraint. This was achieved by covalently modifying peptides with a reagent specific for cysteine-containing peptides and that incorporates a non-native chemical element into the peptide such that the normal or expected isotope pattern for the peptide was changed. The process encodes the peptide with an isotope-distribution encoded tag (IDEnT) that can be decoded by high-resolution mass spectrometry. Once the IDEnT labeled peptide is decoded by visual inspection or computer algorithm analysis, then the parent protein identity can be determined by searching sequence databases with the accurately measured peptide mass and the cysteine constraint.

The IDEnT concept can be used as described above in the field of proteomics for the rapid identification of proteins. However, in another embodiment of the present invention, IDEnT labels can be incorporated into chemical reagents with target specificities for functional groups present in any class of chemical compound including, but not limited to, deoxyribonucleic acid (DNA), ribonucleic acid (RNA), carbohydrates, lipids, proteins, surfactants, detergents and common polymers such as high density polyethylene. The non-native isotopic tag allows the IDEnT labeled analyte to be selectively detected in a mixture without prior knowledge of the m/z ratio or molecular weight. It uses known chemical reactivities or enzymatic activities to selectively direct the IDEnT label with high specificity to functional groups of interest known to be present in a given class of analyte. In addition, chemical compounds can be designed so that the IDEnT is incorporated during synthesis of a compound rather than after synthesis through selective chemical reaction with an IDEnT reagent. The selective incorporation of IDEnTs into biomolecules is expected to find wide application in the analysis of mixtures where detection and isolation of analytes with specific structural features can be accomplished using high-resolution mass spectrometry and/or tandem mass spectrometry.

BRIEF DESCRIPTION OF THE DRAWINGS

FIGS. 3A, 3B and 3C depict observed Mass Spectrometric Data for laminin B1 peptide labeled with the chlorine IDEnT, 2,4dichlorobenzyl-iodoacetamide, and digested with trypsin (FIG. 3A). Expanded scale isotope pattern for (FIG. 3B) [M+2H]2+ion of laminin B1 tryptic peptide Arg Try Val Val Leu Pro Arg Pro Val Cys Phe Glu Lys (SEQ ID NO:1) derivatized at cysteine with chlorine IDEnT and (FIG. 3C) [M+H]1+ ion for the laminin B1 tryptic peptide Gly Met Asn Tyr Thr Val Arg.

FIGS. 4A, 4B and 4C illustrate analysis of a yeast lysate. Yeast proteins, alkylated with 2,4-dichlorobenzyliodoacetamide, were separated by SDS gel electrophoresis, visualized by silver staining and digested by trypsin (FIG. 4A). Band 7 is indicated in FIG. 4A. FIG. 4B is a mass spectrum (single acquisition) from the $\mu$LC-ESI-FTICR-MS analysis from band 7 (FIG. 4A). FIG. 4C is an expanded scale of the mass region indicated in FIG. 4B of a cysteine-containing peptide labeled with the chlorine IDEnT.

DESCRIPTION OF THE PREFERRED EMBODIMENT

Figure 1A:
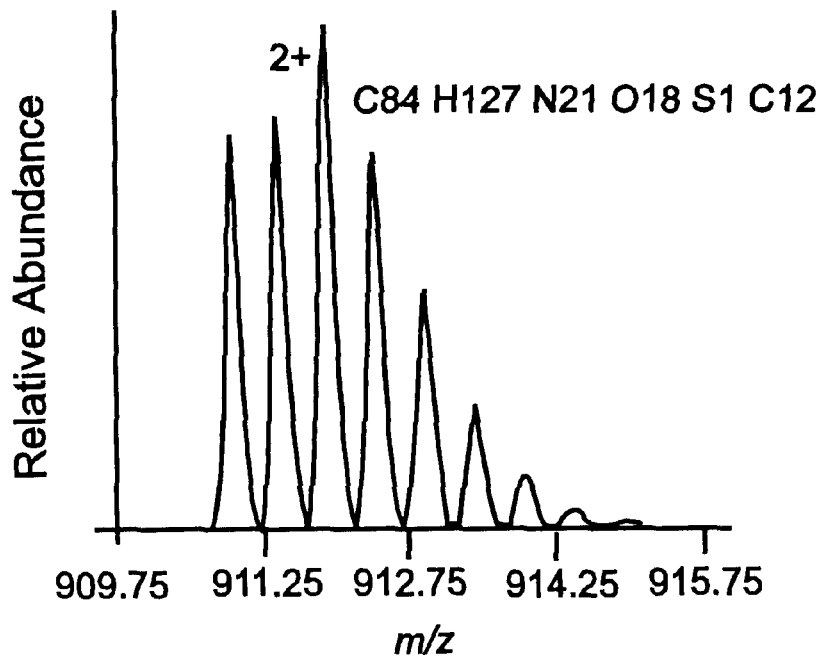
FIGS. 1A and 1B depict an isotope distribution modeled at resolution (m/$\Delta$m @ 1000u) of 5000 for the [M+2H]$^{2+}$ ion of the peptide Arg Tyr Val Val Leu Pro Arg Pro Val Cys Phe Glu Lys (SEQ ID NO:1) with (FIG. 1A) and without (FIG. 1B) chlorine IDEnT.

The present invention describes a method for identifying specific masses of compounds in a complex mixture using an IDEnT strategy or concept. The IDEnT strategy has as its basic tenant the ability to distinguish an analyte encoded with a non-native isotope from those not encoded with the isotope or from those encoded with a different isotope by virtue of their individual isotopic signature(s) in a mass spectrometer. This allows the isotopically encoded or IDEnT labeled analyte(s) to be easily identified in a mass spectrometer. The methods of the present invention involve introduction of a unique isotopic signature into an analyte or chemical compound such that the native isotopic distribution is altered by the presence of the IDEnT. This unique, non-native, isotopic distribution encodes the selected compound with a pattern that can be interpreted by high-resolution mass spectrometry. The IDEnT can be introduced via selective chemical reactions dependent on the target chemistry. Many different types of IDEnT reagents can be synthesized based on the chemistry of the target compound and many different isotopes can be used to create a unique isotopic distribution. Suitable examples of some alternative isotopes are provided in Table 1.

The reagent used for the IDEnT strategy would normally consist of two parts: 1) a chemical element with a unique isotope distribution (see Table 1) not normally found in the analyte class being studied and chemically bonded to an integral part of 2) a chemical reagent with high selectivity or affinity for some specific functional group in the analyte. The two parts are normally linked by covalent bonds, but noncovalent addition of an IDEnT is possible. The simplest form of IDEnT would be a metal ion that binds a specific functional group with high affinity and selectivity such as $Fe^{3+}$ binding to phosphate in a phosphoprotein.

TABLE 1

Examples of Elements Compatibility with the IDEnT Concept

| Element Name | # of Isotopes | Isotope Masses | Natural Abundance of Each Isotope |
|---|---|---|---|
| Li | 2 | 6.015121 | 0.075 |
|  |  | 7.016003 | 0.925 |
| B | 2 | 10.012937 | 0.199 |
|  |  | 11.009305 | 0.801 |
| Mg | 3 | 23.985042 | 0.7899 |
|  |  | 24.985837 | 0.1000 |
|  |  | 25.982593 | 0.1101 |
| K | 3 | 38.963707 | 0.932581 |
|  |  | 39.963999 | 0.000117 |
|  |  | 40.961825 | 0.067302 |
| Ti | 5 | 45.952629 | 0.080 |
|  |  | 46.951764 | 0.073 |
|  |  | 47.947947 | 0.738 |
|  |  | 48.947871 | 0.055 |
|  |  | 49.944792 | 0.054 |
| Cr | 4 | 49.946046 | 0.04345 |
|  |  | 51.940509 | 0.83790 |
|  |  | 52.940651 | 0.09500 |
|  |  | 53.938882 | 0.02365 |
| Fe | 4 | 53.939612 | 0.0590 |
|  |  | 55.934939 | 0.9172 |
|  |  | 56.935396 | 0.0210 |
|  |  | 57.933277 | 0.0028 |
| Ni | 5 | 57.935346 | 0.6827 |
|  |  | 59.930788 | 0.2610 |
|  |  | 60.931058 | 0.0113 |
|  |  | 61.928346 | 0.0359 |
|  |  | 63.927968 | 0.0091 |
| Cu | 2 | 62.939598 | 0.6917 |
|  |  | 64.927793 | 0.3083 |
| Zn | 5 | 63.929145 | 0.486 |
|  |  | 65.926034 | 0.279 |
|  |  | 66.927129 | 0.041 |
|  |  | 67.924846 | 0.188 |
|  |  | 69.925325 | 0.006 |
| Ga | 2 | 68.925508 | 0.60108 |
|  |  | 70.924700 | 0.39892 |
| Ge | 5 | 69.924250 | 0.205 |
|  |  | 71.922079 | 0.274 |
|  |  | 72.923463 | 0.078 |
|  |  | 73.921177 | 0.365 |
|  |  | 75.921401 | 0.078 |
| Se | 6 | 73.922475 | 0.009 |
|  |  | 75.919212 | 0.091 |
|  |  | 76.919912 | 0.076 |
|  |  | 77.9190 | 0.236 |
|  |  | 79.916520 | 0.499 |
|  |  | 81.916698 | 0.089 |
| Br | 2 | 78.918336 | 0.5069 |
|  |  | 80.916289 | 0.4931 |
| Kr | 6 | 77.914 | 0.0035 |
|  |  | 79.916380 | 0.0225 |
|  |  | 81.913482 | 0.116 |
|  |  | 82.914135 | 0.115 |
|  |  | 83.911507 | 0.570 |
|  |  | 85.910616 | 0.173 |
| Rb | 2 | 84.911794 | 0.7217 |
|  |  | 86.909187 | 0.2783 |
| Sr | 4 | 83.913430 | 0.0056 |
|  |  | 85.909267 | 0.0986 |
|  |  | 86.908884 | 0.0700 |
|  |  | 87.905619 | 0.8258 |
| Zr | 5 | 89.904703 | 0.5145 |
|  |  | 90.905644 | 0.1122 |
|  |  | 91.905039 | 0.1715 |
|  |  | 93.906314 | 0.1738 |
|  |  | 95.908275 | 0.0280 |
| Mo | 7 | 91.906808 | 0.4184 |
|  |  | 93.905085 | 0.0925 |
|  |  | 94.905840 | 0.1592 |
|  |  | 95.904678 | 0.1668 |
|  |  | 96.906020 | 0.0955 |
|  |  | 97.905406 | 0.2413 |
|  |  | 99.907477 | 0.0963 |
| Ru | 7 | 95.907599 | 0.0554 |
|  |  | 97.905287 | 0.0186 |
|  |  | 98.905939 | 0.127 |
|  |  | 99.904219 | 0.126 |
|  |  | 100.905582 | 0.171 |
|  |  | 100.904348 | 0.316 |
|  |  | 103.905424 | 0.186 |
| Pd | 6 | 101.905634 | 0.0102 |
|  |  | 103.904029 | 0.1114 |
|  |  | 104.905079 | 0.2233 |
|  |  | 105.903478 | 0.2733 |
|  |  | 107.903895 | 0.2646 |
|  |  | 109.905167 | 0.1172 |
| Ag | 2 | 106.905092 | 0.51839 |
|  |  | 108.904757 | 0.48161 |
| Cd | 8 | 105.906461 | 0.0125 |
|  |  | 107.904176 | 0.0089 |
|  |  | 109.903005 | 0.1249 |
|  |  | 110.904182 | 0.1280 |
|  |  | 111.902758 | 0.2413 |
|  |  | 112.904400 | 0.1222 |
|  |  | 113.903357 | 0.2873 |
|  |  | 115.904754 | 0.0749 |
| Sb | 2 | 120.903821 | 0.574 |
|  |  | 122.904216 | 0.426 |
| Te | 8 | 119.904048 | 0.00095 |
|  |  | 121.903054 | 0.0259 |
|  |  | 122.904271 | 0.00905 |
|  |  | 123.902823 | 0.0479 |
|  |  | 124.904433 | 0.0712 |
|  |  | 125.903314 | 0.1893 |
|  |  | 127.904463 | 0.3170 |
|  |  | 129.906229 | 0.3387 |
| Xe | 9 | 123.905894 | 0.0010 |
|  |  | 125.904281 | 0.0009 |
|  |  | 127.903531 | 0.0191 |
|  |  | 128.904780 | 0.264 |
|  |  | 129.903509 | 0.041 |
|  |  | 130.905072 | 0.212 |
|  |  | 131.904144 | 0.269 |
|  |  | 133.905395 | 0.104 |
|  |  | 135.907214 | 0.089 |
| Ba | 7 | 129.906282 | 0.00106 |
|  |  | 131.905042 | 0.00101 |
|  |  | 133.904486 | 0.0242 |
|  |  | 134.905665 | 0.06593 |
|  |  | 135.904553 | 0.0785 |
|  |  | 136.905812 | 0.1123 |
|  |  | 137.905232 | 0.7170 |
| Eu | 2 | 150.919847 | 0.478 |
|  |  | 152.921225 | 0.522 |
| Re | 2 | 184.952951 | 0.3740 |
|  |  | 186.955744 | 0.6260 |
| Ir | 2 | 190.960584 | 0.373 |
|  |  | 192.962917 | 0.627 |
| Pt | 6 | 189.959917 | 0.0001 |
|  |  | 191.961019 | 0.0079 |
|  |  | 193.962655 | 0.329 |
|  |  | 194.964766 | 0.338 |
|  |  | 195.964926 | 0.253 |
|  |  | 197.967869 | 0.072 |
| Tl | 2 | 202.972320 | 0.29524 |
|  |  | 204.974401 | 0.70476 |
| Pb | 4 | 203.973020 | 0.014 |
|  |  | 205.974440 | 0.241 |
|  |  | 206.975872 | 0.221 |
|  |  | 207.976627 | 0.524 |

In one particular embodiment of the present invention the IDEnT strategy can be used for protein identification. The method described allows for the rapid and unambiguous identification of proteins by sequence database searching using the accurate mass of a single peptide and specific sequence constraints (e.g., the presence of a rare amino acid). Peptide masses can be measured using Fourier Transform Ion Cyclotron Resonance-Mass Spectrometry (FTICR-MS) to an accuracy of 1 ppm (Marshall et al. (1998) Mass. Spectrom. Rev. 17:1–35, incorporated herein by reference). Note however, that FTICR-MS instrumentation is not necessary, but any mass spectrometer with high enough mass resolution to decode the IDEnT can be used. Use of this specific embodiment of the present invention for protein identification also requires a mass spectrometer capable of accurate mass measurement like, but not exclusive to, FTICR-MS. In one particularly preferred embodiment of the present invention, the presence of a cysteine residue within a peptide sequence was used as a sequence constraint. Cysteine is particularly preferred because it is one of three uncommon amino acids. The others, methionine and tryptophan, are also particularly preferred for use in the present invention. Cysteine-containing peptides were detected within a mixture of peptides by incorporating chlorine into a general alkylating reagent specific for cysteine residues. It should be noted that any given amino acid might be uncommon in proteins of a particular type or from a particular source. Thus, dependent upon the type(s) of proteins to be analyzed, selectively labeling of any given amino acid that was uncommon in the proteins to be analyzed could be used in this method.

Figure 1B:
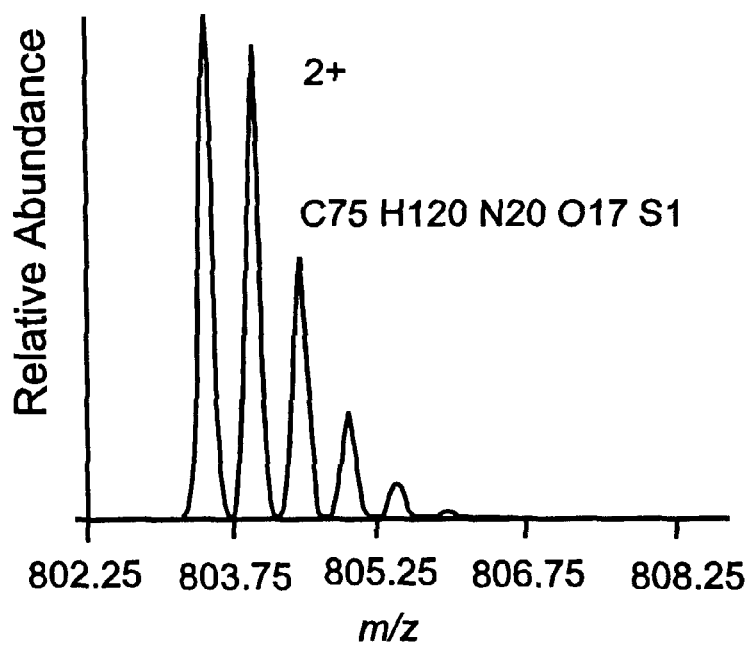

While a reagent for selective incorporation of the IDEnT at cysteine residues in proteins is presented as a specific embodiment of the present invention, other reagents can be used to selectively incorporate the IDEnT at cysteine. Examples of other reagents that can be used to selectively label or tag cysteine include 4-vinylpyridine, iodoacetic acid and acrylamide. Deuterated acrylamide [2,3,3'-De] acrylamide could, for example, be employed. The natural chlorine isotope distribution tagged the cysteine-containing peptide with a pattern recognizable by high-resolution mass spectrometry. The cysteine containing peptide can then easily be identified in a mixture of peptides by virtue of the chlorine IDEnT because peptides do not normally contain chlorine. FIGS. 1A and 1B depict, by modeling, an isotopic distribution for a peptide $[M+H]^{2+}$ ion with and without a chlorine IDEnT. The ability to identify proteins by the accurate mass of a single peptide represents a significant advance in proteome technology (Marshall et al., supra).

Figure 2A:
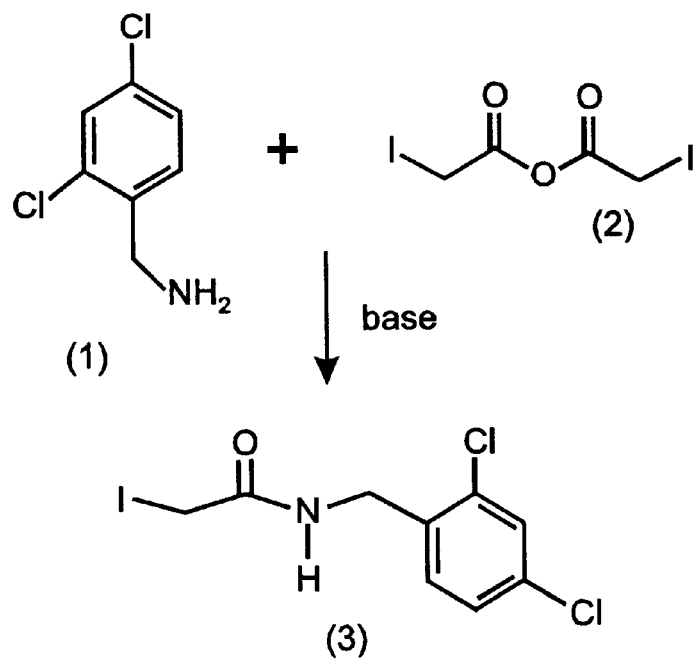
FIGS. 2A and 2B depict a synthesis of an alkylating IDEnT, 2,4 dichlorobenzyl-iodoacetamide, and reaction with free SH group of a protein.
Figure 2B:
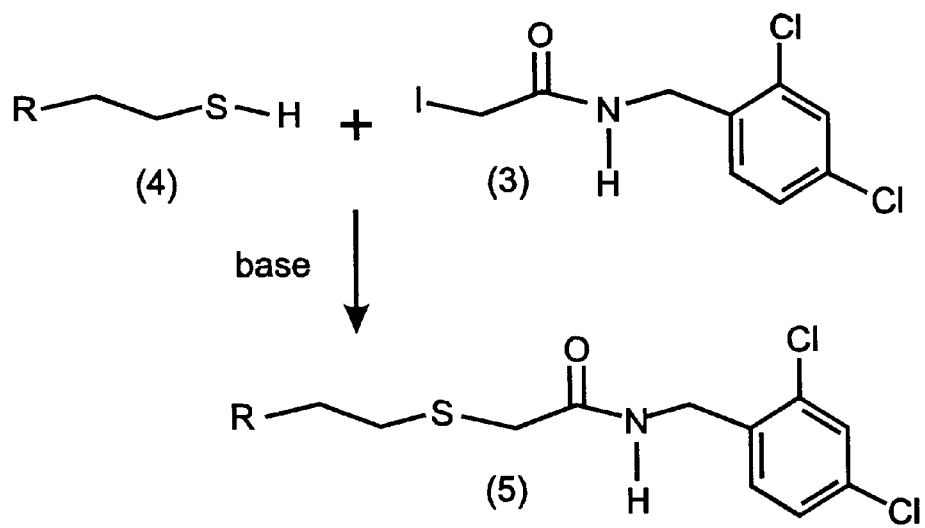

A preferred structure and suitable chemical route for the synthesis of an alkylating IDEnT reagent is provided in FIGS. 2A and 2B. The preferred reagent, 2,4 dichlorobenzyl-iodoacetamide, consists of an iodoacetyl functionality that reacts specifically with the cysteine sulfhydryl at alkaline pH. The benzyl portion of the molecule should contain at least one atom of chlorine, but two to four atoms of chlorine can be used to increase the intensity of the isotope affect. The reaction of the reagent with cysteine is based on general alkylation reagents such as iodoacetic acid or iodoacetamide that have been historically used to derivatize cysteine residues in proteins. In a preferred embodiment, the cysteine-alkylating IDEnT is made by adding half a molar excess of iodoacetic anhydride (1) to a 500 mM solution of 2,4-dichlorobenzylamine (2) in N,N-dimethylforrnamide. The mixture was stirred in the dark for a total of two hours. At 30 and 60 minutes after initial mixing, an equimolar amount of N,N-diisopropylamine was added. After two hours, the reaction mixture was evaporated to dryness, redissolved in acetonitrile/water and purified by reversed-phase HPLC. It should be noted that to use the cysteine constraint any reagent chemistry that is highly specific for cysteine can be used such as vinyl pyridine or maleimide chemistry, both of which would involve different chemical routes for modification to be used as novel IDEnTs with specificity for cysteine.

In a particularly preferred method for protein identification using IDEnT disulfide bonds within proteins are reduced chemically to reactive free SH groups. Reducing reagents include β-mercaptoethanol, dithiothreitol, tri-n-butylphosphine, and the like. This step can be carried out in the presence of solubilizing agents including high concentrations of urea and detergents to maintain protein solubility.

Free SH groups can be derivatized by reaction with a 2-fold Molar excess of 2,4 dichlorobenzyl-iodoacetimde (3) by known methods. For example, for two hours in the dark, labeled proteins can be purified by SDS-PAGE, size exclusion chromatography, reversed phase HPLC, or any other separation method known to the skilled artisan.

Labeled proteins can be digested by proteolysis with, for example, a specific endopeptidase, such as the preferred enzyme trypsin, or by chemical means such as cyanogen bromide. Any process, chemical or enzymatic, that cuts proteins into peptides with high selectivity for the cut site is compatible with the procedure because this cut site is also used as a search constraint. Many such methods are well known to the skilled artisan and can be used in the present invention.

The peptides obtained can be analyzed by introduction into a mass spectrometer using any of a number of methods such as electrophoresis, chromatography, infusion or the like for example, but not limited to, separation on-line, simple infusion, or deposition on a surface. The type of ionization process is not critical, but the mass spectrometer must be capable of high mass resolution.

The method of this invention employs mass spectrometric instruments that have high mass resolution and high accuracy. It is, of course, most preferred to employ instrumentation with the highest resolution and accuracy available. Present instrumentation can have accuracy as high as 0.1 ppm at $1000\mu$. In general, however, the method can employ instrumentation with accuracy higher than about 10 ppm at $1000\mu$. Preferred instrumentation has accuracy higher than or equal to 2.0 ppm $1000\mu$.

In general, the method of this invention should have resolution (m/Δm) of at least about 5,000 @ $1000\mu$. Preferred instrumentation has mass resolution (m/Δm) of about 10,000 @ $1000\mu$ or higher.

FTICR-MS and magnetic sector instruments are capable of achieving the high mass resolution and accuracy to facilitate practice of the invention. Time of flight-based instruments may also be capable of achieving sufficiently high accuracy if a good mass calibration method is employed.

Spectra can be acquired in full scan or single stage mode. Peptides labeled by the IDEnT chemistry are determined by visual inspection of the isotope pattern or by a computer algorithm.

Proteins are identified by comparing the accurately measured mass of the IDEnT labeled peptide after correction for the mass of the IDEnT label to a list of peptides generated by digestion of known proteins with trypsin. If the measured m/z does not result in a unique mass match with the list of tryptic peptides from the database, then certain constraints are applied; for example, 1) remove from the list all peptides that do not contain cysteine; 2) remove from the list all peptides whose unfragmented parent protein is not close in molecular weight to that of the unknown protein; 3) remove from the list all peptides that would not result from complete tryptic digestion of the parent protein. Results from such an application as described above are discussed in the examples and are depicted in FIGS. 3A–3D and Table 2.

Databases of masses of peptide fragments from selective digestion (e.g., with trypsin) of known proteins are available from various sources (e.g., the TIGR Microbial Database web site tigr.org. A database of peptide fragment masses of any given known protein selectively digested by any known method can be readily compiled employing MS methods well-known in the art.

whose masses are measured accurately will provide additional powerful constraints for protein identification from a sequence database. This method would be particularly useful in the protein being identified in a database. It provides a subset of masses that arise specifically from the parent or IDEnT labeled peptide and thus additional constraints. This general approach without any sort of isotopic tag along with mass measurements on a low resolution mass spectrometer is generically referred to as sequence tagging (Susin et al. (1999) Nature 397:441–446, incorporated herein by reference.)

TABLE 2

Yeasts Tryptic Peptides Isobaric with RYVVLPRPVCFEK

| Protein Name[a] | Protein Mass* | Peptide Isobars | Peptide Mass | Error (ppm) |
|---|---|---|---|---|
| Laminin fragment | 2,426.271 | RYVVLPRPVCFEK SEQ ID NO: 1 | 1604.886[#] | 0.189 |
| TPII | 26,778.962 | FLASKLGDKAASELR SEQ ID NO: 2 | 1604.889 | 1.747 |
| YPR143W | 52,661.268 | DKKRTRKNAEFGR SEQ ID NO: 3 | 1604.886 | 0.07 |
| TDR428C | 52,785.179 | NLYDAVSNITRLVK SEQ ID NO: 4 | 1604.889 | 1.747 |
| TAP42 | 31,135.369 | IELFQRNKEISTK SEQ ID NO: 5 | 1604.889 | 1.747 |
| CYC2 | 37,692.826 | VQLKIFETDRQTK SEQ ID NO: 6 | 1604.889 | 1.747 |
| MFS1 | 46,151.311 | ESHPVGILRDLIEK SEQ ID NO: 7 | 1604.889 | 1.747 |
| YMR291W | 64,850.898 | EFDLLRSISEKIR SEQ ID NO: 8 | 1604.889 | 1.747 |
| YKR078W | 51,708.695 | IRTAEDEYRIVLK SEQ ID NO: 9 | 1604.889 | 1.747 |
| TFC6 | 75,311.526 | DKIERIYGLNKEK SEQ ID NO: 10 | 1604.889 | 1.747 |
| SSE1 | 77,318.483 | YLAKEEEKKQALR SEQ ID NO: 11 | 1604.889 | 1.747 |
| YBR102C | 85,484.685 | LDEFIKKNSDKIR SEQ ID NO: 12 | 1604.889 | 1.747 |
| STB6 | 88,779.841 | KISADLNKIDGLYR SEQ ID NO: 13 | 1604.889 | 1.747 |
| FZ01 | 97,746.957 | EKNGFNIEKKALSK SEQ ID NO: 14 | 1604.889 | 1.747 |
| SEC10 | 100,279.455 | NESKIVKRVFEEK SEQ ID NO: 15 | 1604.889 | 1.747 |
| YLL005C | 102,103.872 | IKELLFELFYYK SEQ ID NO: 16 | 1604.885 | 0.234 |
| S5144I | 105,161.643 | HTVTELKSEIHALK SEQ ID NO: 17 | 1604.889 | 1.747 |
| PEX1 | 117,202.758 | EEVKDIIERHLPK SEQ ID NO: 18 | 1604.889 | 1.747 |
| RRP5 | 193,015.955 | AKDKKKVEDLFER SEQ ID NO: 19 | 1604.889 | 1.747 |
| DOP1 | 194,565.002 | LTSSLSPALPAGVHQK SEQ ID NO: 20 | 1604.889 | 1.747 |

*Observed mass whereas all other masses are calculated monoisotopic.
[a]Protein names are as found in the YPD database at www.proteome,com (Hodges, P. E. et al. (1999) Nucl. Acids Res. 26:69–73)
[#]Calculated protein monoisotopic molecular weight.

In still a further embodiment, the use of an IDEnT label of the present invention is provided by accurate mass measurement of just one fragment ion from the IDEnT labeled peptide. Immediately after mass measurement, or in a subsequent analysis, the labeled peptide is isolated or purified in a mass spectrometer. When the IDEnT labeled peptide is isolated, it is subject to fragmentation, depending on the type of mass spectrometer, such that the observed m/z values of the fragment ions correspond to peptide fragments arising from the IDEnT labeled peptide and none other. There is no need to interpret the fragment ions in regard to the sequence of the peptide although this would provide additional constraints. Rather only a few fragment ions In yet another embodiment, IDEnT methods of the present invention can be used for Isotopic Data Dependent Ion Selection. As an example of software for data dependent ion selection Finnigan's (ThermoQuest, San Jose, Calif.) commercially available ion trap instrument allows isotope directed data dependent ion selection. This software can be used with IDEnT chemistry to pretarget a subset of analytes in a mixture for CID. In many cases of mixture analysis, as with phosphopeptides for instance, the analyte of interest is present at much lower abundance than the average analyte and thus is never selected for CID. By using IDEnT chemistry the data-dependent ion selection can be directed toward only those ions with the isotopic tag.

In another embodiment the IDEnT methods of the present invention can be used in the discovery of new enzymes with specific functions. For example, Caspases (ICE or interleukin I converting enzyme) are irreversibly and selectively inhibited by inhibitors referred to as ICE inhibitors that have the general structure Z-VAD-LG where Z is a primary amine protecting group, VAD is for the tripeptide valyl-alanyl-aspartic acid and LG is for any of a number of different leaving groups like chloromethylketone. In order to discover new caspases using the methods of the present invention, one would treat a lysate with a given ICE inhibitor that had IDEnT chemistry incorporated into it and that then tags the active site of caspases with the Z-VAD portion of the inhibitor. The IDEnT incorporated into the Z-VAD moiety remains covalently linked to the enzyme. The lysate is then digested with trypsin and analyzed by MS. Ions exhibiting the IDEnT isotope tag are, because of the known specificity of the ICE inhibitors, proteins that are either caspases of known sequence and in a database, caspases not identified before, or enzymes with caspase like activity.

To determine whether or not there are any unknown caspases present in the pool, a database of caspase sequences can be constructed and a list of peptides from all possible tryptic cleavages in the database can be generated. All the IDEnT tagged peptide masses can then be correlated with the masses in the database. All masses that match a mass in the database are considered to be caspases of known sequence and are not further characterized. Those IDEnT labeled peptides with masses that do not match one in the caspase database can then be sequenced by MS/MS and those sequences searched against an EST database.

With the sequence for a portion of the novel caspase known, polymerase chain reaction (PCR) technology, for example, can then be used to pull out the DNA and the recombinant caspase prepared for characterization. This same approach can be used for other classes of enzymes for which there exist irreversible inhibitors that can be synthesized with the IDEnT chemistry incorporated into that portion of the inhibitor that remains covalently attached to the enzyme. Also this approach can be used to study nonenzymatic proteins that bind a substrate or cofactor with high selectivity. Alternatively, cells can be grown on media containing a specific IDEnT reagent that would be incorporated selectively into cellular molecules like, but not limited to, proteins by the natural enzymatic machinery of the cell. The cells can then be harvested, lysed, cellular proteins solubilized, digested accordingly and mass spectrometry used to find the IDEnT labeled peptides for further characterization by accurate mass measurement or tandem MS.

In a further embodiment, IDEnT methods and chemistry of the present invention can be used for enzyme active site identification. IDEnT chemistry can be incorporated into irreversible enzyme inhibitors like transition state or suicide analogs or reagents. These inhibitors form covalent bonds to the enzyme active site. The IDEnT chemistry provides a means for rapid identification of an enzyme active site in a mixture. This would be particularly useful for active site sequence analysis of an enzyme that has not previously been sequenced, but for which irreversible inhibitors are available. An advantage to the methods of the present invention is that there is usually very little protein available for sequence analysis.

The present methods reduce or eliminate protein losses from a chromatographic purification step so that the active site can be detected and subjected to CID. By incorporating IDEnT chemistry into reagents for peptide sequencing by CID, the IDEnT labels can be used to tag each end of a peptide with a different IDEnT reagent and thus rapidly identify b-ions (i.e., amino terminus) from y-ions (carboxyl terminus). For example, a primary amine directed reagent like acetic anhydride which labels primary amines can allow the IDEnT reagent with a different isotope pattern in a reagent that methylates the carboxyl-terminus can be used to identify the y-ions.

The use of IDEnT methods and reagents of the present invention has as its basic tenant the ability to distinguish an analyte encoded with a non-native isotope from those not encoded with the isotope, or from those encoded with a different isotope by virtue of their individual isotopic signature(s) in a mass spectrometer. This allows the isotopically encoded analyte(s) to be easily identified in a mass spectrometer and provides advantages in a number of applications other than the one presented herein for protein identification by sequence database searching. There are a number of elements that produce isotopes compatible with the IDEnT concept. Some examples of isotopes compatible with the methods of the present invention are listed in Table 1.

In general, if a specific element such as chlorine that exhibits a distinctive isotopic pattern cannot be incorporated into a reagent, then a differential isotopic tag can be introduced by labeling with a mixture of two reagents that are substantially chemically identical, but which differ in the addition of heavy isotopes (such as deuterium) in place of one or more atoms in one reagent. Preferred mixtures contain about a 1:1 molar ratio of the two reagents.

The pair of reagents (light and heavy) exhibit identical reactivity with respect to the labeling reaction. The labeled fragments are identified by detecting pairs of peaks that differ from each other by the mass difference of the light and heavy reagents. Heavy isotopes include, for example, deuterium (substituted for hydrogen) and $^{13}C$ substituted for $^{12}C$.

Carboxylate functionality in proteins and peptides can be specifically labeled using any of a variety of esterifaction chemistries, for example, a methanolic HCl solution prepared using acetyl chloride in methanol. To generate an isotope tag, a first reagent solution is prepared with methanol and a second reagent solution is prepared with deuterated methanol. The two reagent solutions are mixed and used for labeling.

Primary amines such as found at the amino terminus of peptides and proteins and at the amino acid lysine can be readily peracetylated using acetic anhydride. A mass tag is created by labeling using a mixture of acetic anhydride and a deuterated form of acetic anhydride (preferably 1:1).

Noncovalent IDEnT reagents can be used for identification of phosphopeptides. For identification of phosphopeptides of unknown m/z in a mixture of nonphosphorylated peptides, metal ions with a negative mass defect like chromium and ferric iron that have an affinity for phosphate can be added to a mixture of peptides and phosphopeptides. Analysis under gentle ionization conditions that maintain the electrostatic bond between phosphate and metal ions will tag phosphopeptides with a negative mass defect readily observed by high resolution mass spectrometry. Electrostatic bonding interactions are know to be more easily maintained in the gas phase than hydrophobic interactions allowing the [M+Cr]+ ion to be observed selectively over other nonchromium-containing ions. Therefore, phosphopeptides of unknown m/z can be identified and selected for CID in one analytical step. Gallium which does not have a negative mass defect can also be used in place of ferric iron or chromium because it produces an isotope distribution similar to chlorine.

Use of an IDEnT reagent that tags cysteine-containing peptides with an isotopic tag can allow rapid identification of all cysteine-containing peptides and an accounting of all cysteine-containing peptides in complex mixtures or single protein digests where disulfide mapping is of interest. Also, treatment of a native protein with an isotopic tagging reagent of the present invention followed by denaturation and treatment with a second tagging reagent of different mass from the first can allow for a distinction to be made between free cysteines and cysteines bonded to a second cysteine by way of a disulfide bond in the native protein. In this embodiment, the cysteine-containing peptides of interest can be easily distinguished from noncysteine-containing proteins, allowing tandem mass spectrometry to be carried out for the purpose of sequencing the peptide.

The IDEnT reagents and methods of the present invention can also be used to do relative-quantitative analysis. In this embodiment, two reagents similar in chemical composition and containing the same or different IDEnTs can be used, wherein one is isotopically enriched with deuterium in place of hydrogen or C-13 in place of C-12, such that the mass of one is greater than the other, but the chemical properties are nearly identical. The use of two such reagents would allow one to do comparative analysis between identical proteins originating from different cellular states. For instance, comparison of proteins from cellular state A with those in state B would comprise, for example, lysing both cell populations and arbitrarily treating the protein in A with the lower mass reagent and those in B with the higher mass reagent. The tagged protein populations are then mixed, digested with a protease, and analyzed by mass spectrometry with some sort of on-line separation technique. Chemically similar peptides will elute simultaneously allowing relative quantitation, such as by area under a curve. One can readily distinguish the IDEnT labeled peptides from the unlabeled peptides and then compare the relative abundance of protein A from cellular state A with protein A from cellular state B.

In a separate embodiment, the method comprises use of the same basic IDEnT reagent structure but one IDEnT would contain 2 chlorines and the other would differ only in that it contained 4 chlorines. The two chemically similar reagents would be distinguishable by the intensity of the chlorine isotope pattern that would be exaggerated in the tagged analyte with the 4-chlorine IDEnT over that with the 2-chlorine IDEnT.

In yet another embodiment of the present invention, a reagent that contains the alkylating specificity for cysteine with the biotin functional group connected by a linker that is modified with IDEnT chemistry can be used. The methods and reagents further comprising biotin, for example, can be used for affinity enrichment of these cysteine-containing peptides by passing them over an avidin column. These reagents provide the following advantages: 1) an isotopic tag to easily identify the isotopically tagged peptides in a mass spectrometer, and 2) the biotin tag to enrich the cysteine tagged peptides. This embodiment of the present invention would also incorporate the use of two different isotopic tagging reagents of different mass so that semi-quantitative or quantitative analysis can be obtained.

IDEnT chemistry of the present invention can also be incorporated into protein cross-linking reagents. In this embodiment, a protein of interest can be cross-linked in order to understand which linear regions of the protein or between two different proteins are juxtaposed in space. The crosslinked proteins are then digested with a protease and the peptides analyzed by mass spectrometry. Using the present methods and reagents, the analyte of interest would not normally be present in a database and the CID from which would likely not be interpretable. Incorporation of IDEnT chemistry into the crosslinking reagent allows the crosslinked peptide to be rapidly detected in the mixture. Knowing the sequence of the protein(s) the masses of the two crosslinked peptides can then be calculated and the crosslinked regions quickly assigned.

Any of various crosslinking agents such as succinimidyl-4-(N-maleimido-methyl) cyclohexane-1-carboxylate, disuccinimidyl suberate, bis maleimidohexane, bis [b-(4-azido salizylamido) ethyl] diisulfide, bis (sulfosuccinimidyl) suberate and dimethyladepimidate can be used to prepare IDEnT tag reagents by incorporation of non-native atoms exhibiting a distinctive isotope pattern or by incorporating heavy isotopes in place of atoms in the reagent.

Further, the incorporation of IDEnT chemistry of the present invention can be incorporated into other biopolymers, for example, into dideoxynucleic acids. Use of the reagents and methods can allow mass spectrometric identification of a chain termination event and potentially lead to ladder sequencing of DNA by, for example, MS methods This invention also relates to compounds that can be employed as IDEnT reagents to label selected functional groups in proteins. Most generally these compounds comprise an element, such as those listed in Table 1, not normally found in proteins (or only rarely found in proteins) that has a distinctive isotope distribution pattern that can be used to identify peaks in a mass spectrum that carry the label. The compound further comprises a reactive group that selectively reacts with a selected functional group in the protein. Compounds that carry reactive groups that selectively react with cysteine, methionine and tryptophan are of particular interest. Additional reactive groups of interest are those that selectively react with primary amine groups or with carboxylic acid groups. In a specific embodiment, the invention relates to IDEnT reagents that comprise one or more chlorine atoms and a reactive group that is selective for reaction with cysteine. More specifically, the invention relates to compounds of the formula:

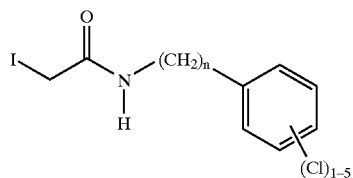

which selectively react with cysteines, where n can be 1–5 and the phenyl ring can be substituted with 1–5 chlorines. Preferred reagents are those in which n is 1 and where 1–4 chlorines are substituted on the ring. IDEnT reagents of this formula include the 2,4-dichloro reagent (3) of FIGS. 2A and 2B.

The invention is further illustrated by the following examples which are not intended to limit the scope of the invention.

EXAMPLES

Reagent Design: A cysteine-specific IDEnT was employed to label and/or detect cysteine-containing peptides within a mixture of peptides predominantly without cysteine. The IDEnT reagent was 2,4-dichlorobenzliodoacetamide. Chlorine was chosen as the isotope tag because it provides an isotopic signature readily discernible by mass spectrometry. The isotopic contribution from two atoms of chloride to a normal peptide isotopic distribution was easily recognized in peptides up to 2000μ, but isotopic modeling was required to confirm the presence of chlorine at higher mass.

Mass Spectrometry: Desalted peptide standard samples were analyzed by direct infusion into an ESI-FTICR-MS using an 11.5 tesla magnet. Conditions for operation of the FTICR-MS were similar to those reported elsewhere and external mass calibration was established with an ESI-FTICR mass spectrum using a peptide mixture generated by tryptic digestion of bovine serum albumin (Bruce, J. A. et al. (1999) Anal. Chem. 71:2595–2599). Mass spectra were obtained each 2.5 seconds using an external quadrupole to store ions prior to injection into the ICR cell.

Complex peptide mixtures from in-gel digestion of yeast proteins were analyzed by microcapillary HPLC ($\mu$LC) using a 50 $\mu$m×10 cm capillary column packed with POROS C18 (PerSeptive Biosystems) using a pressure cell (Mass Evolution, Inc. Houston, Tex.) to slurry pack the column and to load the sample (Lee, N. et al. (1998) J. Immunol. 160:4951–4960; Mosely, M. A. et al. (1991) Anal. Chem. 63:1467–1473). For ESI the $\mu$LC column was connected to a VALCO union (Houston, Tex.) that transferred the column effluent to a New Objective, Inc. (Cambridge, Mass.) glass needle with a 30 $\mu$m tapered tip. Mass spectral data were acquired using an FTICR-MS equipped with a 7 tesla magnet that employed in-trap ion accumulation (i.e., ion injection, pump-down, and excitation/detection) every~3 s (Winter, B. E. et al. (1993) J. Am. Soc. Mass Spectrom. 4:566–577). A new method of calibration was used that enables very high mass measurement accuracy without the requirement for internal calibrants and is described elsewhere (Bruce, J. E. (2000) J. Am. Soc. Mass Spectrom., accepted (See Appendix A)). Tandem mass spectral data of protein digests were acquired using an ion trap (ThermoQuest, San Jose) operated in dynamic exclusion mode (Gygi, S. P. et al. (1999) Mol. Cell. biol. 19:1720–1730).

IDEnT Peptide Detection: Peptides alkylated by reaction with 2,4 dichlorobenzyl-iodoacetamide (IDEnT peptides) were identified either visually or by screening of the data with a computer algorithm that recognized the presence of chlorine in an isotopic distribution. Peptides with masses less than 2000 u had a distinctive isotopic distribution when alkyated with the dichloro-IDEnT reagent. FTICR spectra were processed with software (i.e., ICR-2LS) developed at Pacific Northwest National Laboratory, to automatically detect and report the masses of all IDEnT labeled peaks in a spectrum. The experimental distribution was compared with a theoretical distribution for both labeled and unlabeled peptides. A least square error was calculated between the experimental and both theoretical distributions. Chlorine labeled peaks were considered positively identified when experimental isotopic patterns better fit the theoretical chlorine labeled distributions than the unlabeled distributions.

Protein Identification: Tandem MS spectra of single peptides were analyzed using the software SEQUEST (see U.S. Pat. Nos. 5,538,897 and 6,017,693), which is commercially available from Thermo Quest, San Jose which 1) generates a list of peptides in a database (e.g. OWL) that match the molecular mass of the unknown peptide on which CID was carried out, and then 2) compares the observed CID spectrum of the unknown with that for all possible isobars (Eng, J. et al. (1994) J. Am. Soc. Mass Spectrom. 5:976–989). A correlation score of 2.0 and a cross-correlation score of 0.1 were set as the minimum reliable values for an initial protein screen. These initial positive protein identifications were confirmed by manually checking the CID data for a fit to the identified sequence.

Proteins were also identified by mass mapping of the data acquired by $\mu$LC-ESI-1E FTICR-MS analysis of peptide mixtures. Automated analysis of ESI-FTICR mass spectra using ICR-2LS (available from Pacific Northwest National Laboratory, Richland, Wash.) was coupled with database searching. To identify proteins isolated from *S. cerevisiae*, proteolysis was carried out on all open reading frames according to the rules for protein fragmentation by trypsin (i.e., amide bonds are hydrolyzed leaving lysine or arginine at the new carboxyl-terminus). Mass deconvolution used an algorithm called THRASH (Horn, D. M. et al. (1998), Proceedings of the 46$^{th}$ ASMS Conf. on Mass Spectrometry and Allied Topics, Orlando, Fla. May 31–Jun. 4, 1998, p. 118). The resulting masses were then corrected for the space charge induced frequency shift to increase mass measurement accuracy (Bruce, J. E. et al. (2000) J. Am. Soc. Mass Spectrom., accepted (See Appendix A)). The resulting table of neutral masses was then compared to the table of masses consisting of all possible proteolytic (i.e. tryptic) fragments calculated for the entire yeast genome downloaded from the NCBI web site. Program output was structured as a table of experimentally measured masses and predicted peptides within the defined search criteria (e.g., mass measurement error).

Figure 3C:
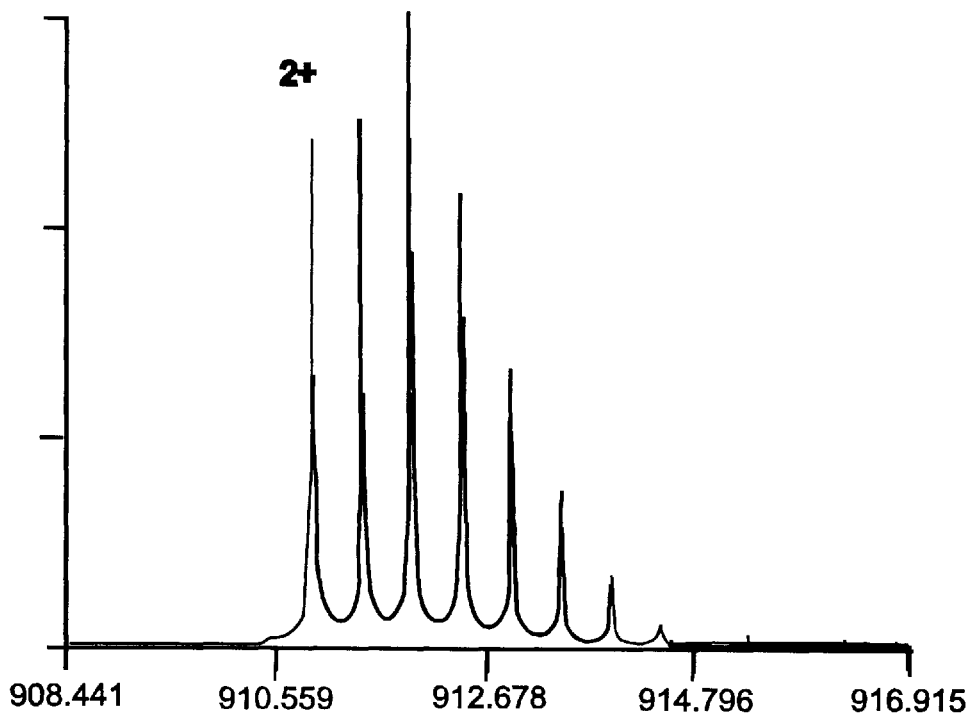
Figure 3D:
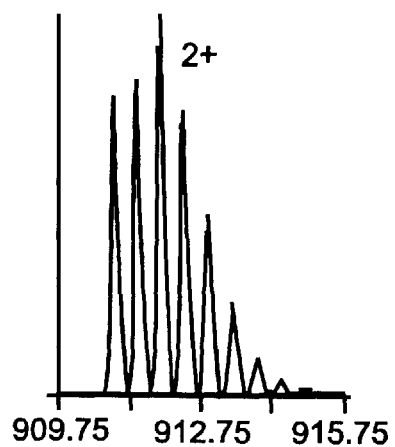
FIG. 3D is the modeled isotopic pattern for peptide RYVVLPRPVCFEK (SEQ ID NO:1) labeled with the IDEnT reagent.

Protein Labeling: A 2-fold molar excess of 2,4-dichlorobenzyliodoacetamide was allowed to react with an alkaline solution (50 mM ammonium bicarbonate) of laminin B1 peptide (Sigma, St. Louis, Mo.) for two hours in the dark. After labeling laminin B1 (RYVVLPRPVCFEKGMNYTVR), SEQ ID NO:21 was digested with trypsin to produce two fragments of which one (RYVVLPRPVCFEK), SEQ ID NO:1 was labeled with the IDEnT reagent and the other (GMNYTVR), SEQ ID NO:22 was not. Prior to MS analyses, the sample was desalted on a C-18 ziptip (Millipore Corp. Bedford, Mass.). The labeled and digested peptide was analyzed by ESI-FTICR-MS. FIG. 3A shows the ESI-FTICR mass spectrum for the labeled and digested laminin B1 and in expanded views, the isotopic distribution of the unlabeled peptide fragment GMNYTVR, SEQ ID NO:22) (FIG. 3B) as well as the IDEnT labeled peptide fragment RYVVLPRPVCFEK, SEQ ID NO:1) (FIG. 3C). Trypsin will not hydrolyze the arginyl-proline peptide bond or the amino- or carboxy-terminal arginyl-tyrosine or valyl-arginine bonds. Trypsin must bind the substrate peptide on both sides of the active site. The presence of chlorine covalently bonded to labeled peptide was readily apparent on comparison of the observed mass spectrum (FIG. 3C) and a modeled mass spectrum of the same peptide sequence with the IDEnT label attached (FIG. 3D).

Protein Identification (Model Study): The sequence of the cysteine-containing, laminin B1 peptide fragment (RYVVLPRPVCFEK), SEQ ID NO:1 produced by tryptic digestion of laminin B1 peptide was introduced into a database downloaded from the NCBI web site containing all yeast open reading frames. For each IDEnT peptide being studied a list of all possible peptide isobars to the corrected mass was produced by trypsin digestion of all 6,118 yeast proteins (344,855 possible peptide fragments). The list of yeast peptides isobaric for each IDEnT peptide allowed for the presence of missed tryptic cleavage sites, but a lysine or arginine at the carboxyl terminus was required. To identify the protein from which a given IDEnT peptide was derived the following constraints were applied: 1) generate a list of all possible isobaric peptides at an accuracy of 1–2 ppm for each IDEnT peptide with a carboxyl-terminal lysine or arginine, 2) retain peptides with at least one cysteine in their sequence (NOTE: two or more cysteines in an unknown peptide would be distinguished by an enhanced chlorine isotopic pattern and provide a more restrictive constraint than a single cysteine) and 3) retain peptides derived from proteins with a molecular weight that was within+/−1000 u of the average mass of proteins found by mass mapping of the same ESI-FTICR-MS data set.

Of the 344,855 possible peptide fragments that could be generated by complete or incomplete digestion with trypsin. Twenty had masses within 2 ppm of the mass measured for the IDEnT labeled peptide after correction for the weight of the label. This list of 20 peptides indistinguishable by mass measurement alone (Table 2) was reduced to a single and correct answer, the laminin B1 tryptic fragment RYVVL-PRPVCFEK (SEQ ID NO:1), by applying the cysteine constraint. In this case it was not necessary to consider the molecular weight of the parent proteins to arrive at the correct identification. The protein molecular weight would, however, provide an additional and easily obtainable constraint in cases where proteins separated by gel electrophoresis were analyzed.

Protein Labeling: Yeast (K1322) cells were inoculated into 5 mL of media containing raffinose without uracil and expanded to 30 mL after 24 hrs. Cells were then switched to 275 mL of media containing galactose without uracil and harvested at log phase. A lysate was prepared according to previously reported methods (Gygi, S. P. et al. (1999) Mol. Cell. Biol. 19:1720–1730). The lysate was fractionated by ion exchange chromatography on a Q-Sepharose column to reduce the complexity of the mixture such that discrete protein bands were visible after SDS-PAGE separation and sliver staining of a single fraction. Three fractions (1 mg protein total) eluted at ~50 mM sodium chloride were pooled, desalted three times with a Centricon Spin column (Millipore Corp., Bedford, Mass.) using 50 mM ammonium bicarbonate and diluted finally to 370 $\mu$L. After desalting, 20 $\mu$L (or 90 $\mu$g total protein) of the sample was combined with 20 $\mu$L of 3% SDS/0.9 M TRIS, pH 8.5 and 10 $\mu$L of 1 nmole/$\mu$L dithiothreitol. This mixture was boiled for 5 minutes and then 10 $\mu$L of the IDEnT reagent, 2,4 dichlorobenzyl-iodoacetamide (20 nmole/$\mu$L), in 100% acetonitrile was added and allowed to react for 1 hr in the dark at room temperature. Prior to separation by SDS-PAGE the samples was subjected to vacuum concentration (3 min) in a Speedvac to remove excess acetonitrile, and 16 $\mu$L of a solution of glycerol (40%) and bromophenol blue added. Labeled proteins were separated by SDS-PAGE (10% C), detected by silver staining and protein bands of interest were excised/digested in the gel with trypsin (Laemmli, U. K. (1970) Nature 227:680–695; Shevcheiiko, A. et al. (1996) Anal. Chem. 68:850–858).

Figure 4A:
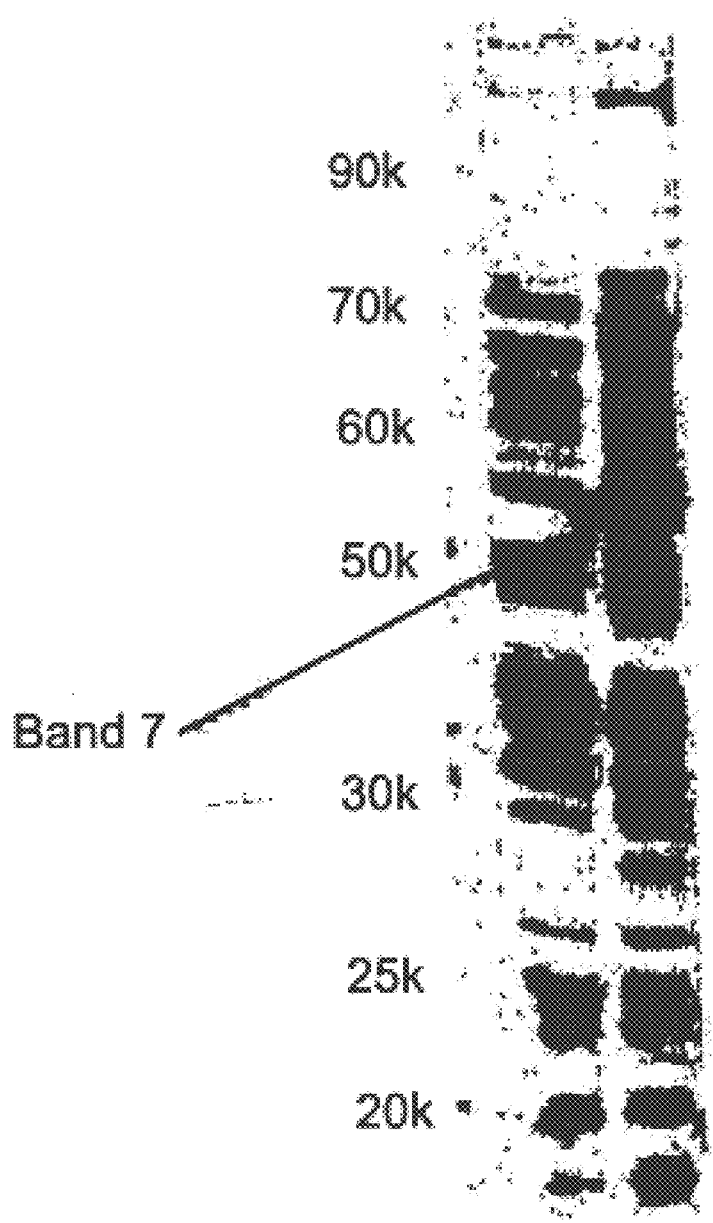

Identification of proteins using the accurate mass of a single cysteine-containing peptide was tested on a complex sample containing proteins from the yeast lysate (described above). However, in order to validate results from this new approach identical aliquots of the same sample were first identified by $\mu$LC-ESI using data acquired by tandem MS on an ion trap and mass mapping with an FTICR-MS. The proteins present in an ion exchange chromatography fraction of total yeast lysate were separated by gel electrophoresis and the proteins in band 7 (FIG. 4A) were analyzed. The tandem MS method identified five proteins with codon bias values ranging from 0.608 to 0.324 (Table 3, Column 2). Proteins with calculated codon bias values in this range are expected to be expressed in yeast at a high abundance. Codon bias values indicate the propensity for a gene to utilize the same codon to encode an amino acid even though other codons would insert the identical amino acid into the growing polypeptide chain (Bennetzen, J. L. and Hall, B. D. (1982) J. Biol. Chem. 257:3026–3031). In yeast cells the value ranges from −0.3 to 1.0 and it is further found empirically that proteins having a large codon bias value (>0.2) are expressed at high levels and proteins expressed at low levels have low codon bias values (<0.1).

TABLE 3

Yeast Proteins Identified by Three Different Methods

| Protein | Tandem MS | Mass Map | IDEnT | Codon Bias | Protein MW |
|---|---|---|---|---|---|
| YML056C | + | + | + | 0.608 | 56,357.72 |
| YLR432W | + | + | + | 0.599 | 56,548.73 |
| CYS4 | − | + | − | 0.444 | 55,987.36 |
| YHR216W | + | + | − | 0.438 | 56,493.85 |
| YOR374W | + | + | − | 0.422 | 56,688.19 |
| AR08 | + | + | + | 0.324 | 56,142.66 |
| ALD5 | − | − | + | 0.262 | 56,585.29 |
| YDR132C | − | − | + | 0.040 | 57,158.03 |
| CLB2 | − | − | + | 0.004 | 56,211.64 |

Next a duplicate of band 7 (FIG. 4A) was digested with trypsin and the peptide masses measured to ~1 ppm by $\mu$LC-ESI-FTICR-MS. The data was analyzed by computer algorithm to identify proteins by mass mapping. Six proteins (Table 2, Column 3) were identified including all five of the proteins identified by the data-dependent tandem NIS approach. All proteins identified by mass mapping had codon bias values that were >0.3 indicating that these proteins were likely to be expressed at a high abundance in the cell. The proteins identified by this method had a calculated average molecular weight of 56,352.60+/−191.73 u that was in good agreement with the estimate by gel electrophoresis.

Finally, proteins were identified by the accurately measured masses of single IDEnT labeled peptides using the same FTICR-MS data set used for the mass mapping analysis. FIG. 4B shows the complex mixture of ions detected in a single acquisition during the $\mu$LC separation of peptides produced by tryptic digestion of the proteins in band 7. All IDEnT labeled peptides were automatically detected by a computer algorithm that compared the observed isotopic pattern (FIG. 4C) with theoretical isotopic patterns for the same mass with and without the IDEnT label. This novel approach identified six proteins (Table 3, Column 4), three of which were also identified by the data-dependent tandem MS method and by the mass mapping method. The three additional proteins identified by accurate mass measurement of IDEnT labeled peptides were YER073W, a protein involved in amino acid metabolism, YDR132C, a protein of unknown function and CLB2, a protein that participates in signal transduction known to be phosphorylated and to contain a zinc finger domain. Based on codon bias values YDR132C and CLB2 can be expected to be expressed at low abundance in yeast (Table 3, Column 5). Such proteins are not usually identified from complex cell lysates by the data-dependent, tandem MS method which is one indicator of the better effective sensitivity achieved by using the accurately measured masses of single, IDEnT labeled peptides to identify proteins (Gygi, S. P. et al. (1999) Mol. Cell.

Biol. 19:1720–1730; Gygi, S. P. et al. (1999) Nature Biotechnol. 17:994–999).

This approach identified more proteins than the data-dependent, tandem MS approach alone (Table 3, Column 2). Furthermore, if the FTICR-MS data set is analyzed as a whole by combining the mass mapping and IDEnT approaches (Table 3, Columns 3 & 4), then nine proteins were identified versus only five by the tandem MS approach alone. None of the proteins identified by the tandem MS approach were missed by such an analysis.

An important aspect of this method is the fact that it allows the identification of low abundance proteins normally missed by a tandem MS method because of the effective loss of dynamic range due to data-dependent analysis. While the two low abundance proteins identified by the accurate mass approach can not be confirmed by the two standard methods there is no reason to expect the method to fail at low signal to noise as long as the mass can be accurately assigned. Identifying proteins using FTICR-MS and thus avoiding CID provided the expected advantages, namely 1) high resolution (>10,000 @ 1000 u) to analyze more complex mixtures than possible with other instruments (the ion trap data set was notable in that only one IDEnT labeled peptide was observed) (Bruce, J. A. et al. (1999) Anal. Chem. 71:2595–2599); and 2) mass accuracy<1.0 ppm, allowing more proteins to be identified by better utilizing more of the information in the data set.

All references cited herein are incorporated by reference herein to the extent not inconsistent herewith.

Those of ordinary skill in the art will appreciate that methods, reagents, analytical techniques, separation processes, methods of data analysis and computer programs for data analysis other than those specifically disclosed here are available in the art and can be readily applied or adapted in view of the disclosures herein to the practice of this invention. The use of all such readily available and applicable methods, reagents and software programs are intended to be encompassed by this invention.

We claim:

1. A method for identifying a peptide or protein in a mixture comprising one or more peptides or proteins which comprises the steps of:
   (a) labeling one or more peptides or proteins in the mixture with a first isotope-distribution tag reagent which comprises an element having an isotope distribution not normally found in the one or more peptides or proteins in the mixture and which selectively reacts and bonds to a functional group in one or more peptides or proteins in the mixture to give one or more labeled peptides or proteins;
   (b) digesting the labeled peptides or proteins in the mixture using a digestion method that is selected to generate one or more digested peptides or proteins from the labeled peptides or proteins in the mixture that are selectively labeled with the first isotope-distribution tag reagent;
   (c) measuring the masses of the digested peptides or proteins selectively labeled with the first isotope-distribution tag reagent employing mass spectrometry to give the masses of digested peptides or proteins selectively labeled with the first isotope-distribution tag reagent; and
   (d) comparing the mass of one and only one single labeled digested peptide or protein determined in step (c) with one or more databases comprising the masses of peptides or proteins generated by digestion of known peptides or proteins using the digestion method of step (b) to identify the peptide or protein in the database from which the single digested peptide or protein is derived and to thereby identify one of the peptides or proteins in the mixture.

2. The method of claim 1 wherein the digestion method is digestion with an endopeptidase.

3. The method of claim 2 wherein the digestion method is digestion with trypsin.

4. The method of claim 1 wherein the isotope-distribution tag reagent selectively reacts with cysteine to label cysteines in one or more peptides or proteins in the mixture with an isotope distribution not normally found in the one or more peptides or proteins in the mixture.

5. The method of claim 1 wherein the isotope-distribution tag reagent selectively reacts with tryptophan to label tryptophan in one or more peptides or proteins in the mixture with an isotope distribution not normally found in the one or more peptides or proteins of the mixture.

6. The method of claim 1 wherein the isotope-distribution tag reagent selectively reacts with methionine to label methionine in one or more peptides or proteins in the mixture with an isotope distribution not normally found in the one or more peptides or proteins of the mixture.

7. The method of claim 1 wherein, in comparing the measured mass of the single digested labeled peptide or protein to those in the database, the presence of the functional group in a labeled peptide is used to exclude peptides in the database from the mass comparison.

8. The method of claim 7 wherein in comparing the measured mass of the single digested labeled peptide or protein to those in the database, the measured or estimated molecular weight of the protein or proteins to be identified is used to exclude peptides in-the database from the mass comparison.

9. The method of claim 1 further comprising labeling one or more peptides or proteins in the mixture with a second isotope-distribution tag reagent which comprises an element having an isotope distribution not normally found in the one or more peptides or proteins of the mixture and different from the element in the first isotope-distribution tag reagent and which selectively reacts with a functional group different from the functional group with which the first isotope-distribution tag reagent reacts.

10. The method of claim 9 wherein the first and second isotope distribution tag reagents are used to tag either end of the one or more peptides or proteins in the mixture.

11. The method of claim 10 wherein the first isotope-distribution tag reagent labels amino termini and the second isotope-distribution tag reagent labels carboxy termini.

12. The method of claim 9 wherein the first and second isotope-distribution tag reagents contain a different number of chlorine atoms.

13. The method of claim 1 wherein the first isotope-distribution tag reagent comprises one or more chlorine atoms.

14. The method of claim 1 wherein the one or more peptides or proteins in the mixture are separated by size, molecular weight or on an affinity column prior to step (a).

15. The method of claim 14 wherein steps (b)–(d) are conducted on separate samples of a given protein mixture employing more than one digestion method.

16. The method of claim 15 wherein the protein is an enzyme and the isotope-distribution tag reagent is an inhibitor of the enzyme.

17. The method of claim 1 wherein the one or more digested peptides or proteins are separated by size, molecular weight or on an affinity column prior to step (c).

18. The method of claim 1 further comprising the step of determining the amino acid sequence of one or more labeled peptides or proteins using collision-induced dissociation mass spectrometry.

19. The method of claim 1 wherein the measurement of the masses of the one or more digested peptides or proteins of step (c) is performed by Fourier Transform Ion Cyclotron-Mass Spectrometry.

20. The method of claim 1 where the first isotope-distribution tag reagent comprises two substantially chemically identical compounds which differ from each other by the substitution of a heavy isotope for at least one atom.

21. The method of claim 20 wherein the heavy isotope is deuterium which is substituted for hydrogen in one of the two reagents.

22. The method of claim 20 wherein the heavy isotope is $^{13}C$ which is substituted for $^{12}C$ in one of the two reagents.

23. The method of claim 1 wherein the isotope-distribution tag reagent binds to an active site or a ligand binding site in the one or more peptides or proteins in the mixture.

24. The method of claim 23 wherein an enzyme is labeled with an isotope distribution tag reagent that is an inhibitor of said enzyme.

25. The method of claim 1 further comprising the step of chemically reducing disulfide bonds in the one or more peptides or proteins in the mixture and wherein the isotope-distribution tag reagent bonds to a free sulihydryl group.

26. The method of claim 1 wherein the one or more peptides or proteins in the mixture are digested using cyanogen bromide.

27. The method of claim 1 which is applied to the identification of proteins in a mixture of proteins.

28. The method of claim 1 wherein the isotope-distribution tag reagent is a mixture of acetyl chloride in methanol and deuterated methanol.

29. The method of claim 1 wherein the mixture of peptides and proteins contains phosphoproteins and the isotope-distribution tag reagent bonds to phosphate groups.

30. The method of claim 29 wherein the isotope-distribution tag reagent comprises metal ions with a negative mass defect which have an affinity for phosphate.

31. The method of claim 1 wherein the isotope-distribution tag reagent alkylates cysteine and contains a biotin functional group.

32. The method of claim 1 wherein the isotope-distribution tag reagent is a protein crosslinking reagent.

33. The method of claim 1 wherein the isotope distribution tag reagent has the formula:

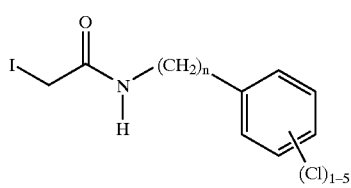

where n is an integer which can be 1–5.

34. The method of claim 33 wherein in the isotope-distribution tag reagent n is 1 and the phenyl ring is substituted with 1–4 chlorines.

35. The method of claim 1 wherein the step of measuring the masses of the one or more digested peptides or proteins is performed using an FT-ICR mass spectrometer.

36. The method of claim 1 wherein the step of measuring the masses of the one or more digested peptides or proteins is performed using a mass spectrometer having a resolution of about 5000 to about 10,000@ $1000\mu$.

37. The method of claim 1 wherein the step of measuring the masses of the one or more digested peptides or proteins is performed using a mass spectrometer having a resolution of about 10,000@ $1000\mu$ or higher.

38. The method of claim 1 wherein the step of measuring the masses of the one or more digested peptides or proteins is performed using a mass spectrometer having an accuracy of about 10 to about 2.0 ppm at $1000\mu$.

39. The method of claim 1 wherein the step of measuring the masses of the one or more digested peptides or proteins is performed using a mass spectrometer having an accuracy of about 2.0 ppm at $1000\mu$ or higher.

40. A method for identifying a protein in a mixture of proteins that is at least in part encoded by a known expressed sequence tag which comprises the steps of:
   (a) labeling a protein in the mixture with a first isotope-distribution tag reagent which comprises an element having an isotope distribution not normally found in the proteins of the mixture and which selectively reacts and bonds to a functional group in a protein to give a labeled protein;
   (b) digesting the labeled protein using a digestion method that is selective for a cut site in the protein to generate digested peptides including peptides that are selectively labeled with the first isotope-distribution tag reagent derived from proteins in the labeled protein mixture;
   (c) measuring the masses of the digested peptides selectively labeled with the first isotope-distribution tag reagent employing mass spectrometry to give the masses of the digested labeled peptides; and
   (d) comparing the mass of one and only one single digested labeled peptide determined in step (c) with one or more databases comprising the masses of peptides encoded by known expressed sequence tags to identify peptides in the database that correspond to the single digested peptide and thereby determine which protein(s) in the mixture are encoded at least in part by a given expressed sequence tag.

41. A method for identifying a peptide or protein in a mixture comprising the steps:
   (a) labeling one or more peptides or proteins in a mixture with an isotope-distribution tag reagent that selectively labels one or more amino acids in one or more peptides or proteins in the mixture to give one or more labeled peptides or proteins;
   (b) determining the masses of the labeled peptides or proteins by mass-spectrometry to give the masses of the peptides or proteins; and
   (c) identifying a peptide or protein in a database using the mass of one and only one single labeled peptide or protein and a sequence constraint derived from the specificity of the first isotope-distribution tag reagent; wherein the mass of the single peptide or protein and the sequence constraint identifies a peptide or protein in the database.

42. The method of claim 41 further comprising digesting the mixture using a digestion method that is selected to generate one or more digested peptides or proteins.

43. The method of claim 42 wherein step (c) is performed without determining the sequence of any ion derived from said one or more labeled peptides or proteins.

44. The method of claim 41 wherein step (c) is performed without -determining the sequence of any ion derived from said one or more labeled peptides or proteins.

45. A method for identifying a peptide or protein in a mixture comprising the steps:
   (a) labeling one or more peptides or proteins in a mixture with an isotope-distribution tag reagent that selectively labels one or-more uncommon amino acids in one or more peptides or proteins in the mixture to give one or more labeled peptides or proteins;
   (b) digesting the mixture using a digestion method that is selected to generate one or more digested labeled peptides or proteins;
   (c) determining the masses of said digested labeled peptides or proteins by mass-spectrometry to give the masses of the digested labeled peptides or proteins; and
   (d) identifying a protein or peptide in a database using the mass of one and only one single digested labeled peptide or protein and a sequence constraint derived from the specificity of the first isotope-distribution tag reagent;
      wherein the mass of the single digested labeled peptide or protein and the sequence constraint identifies a peptide or protein in the database.

46. The method for identifying a peptide or protein in a mixture according to claim 45 wherein the isotope-distribution tag reagent selectively labels an uncommon amino acid selected from cysteine, methionine, or tryptophan.

47. A method for identifying a peptide or protein in a mixture comprising the steps:
   (a) labeling one or more peptides or proteins in a mixture with an isotope-distribution tag reagent that selectively labels one or more amino acids in one or more peptides or proteins in the mixture to give one or more labeled peptides or proteins;
   (b) fragmenting the peptides or proteins in the mixture in a mass spectrometer to generate one or more fragmented peptides or proteins selectively labeled with an isotope-distribution tag reagent;
   (c) determining the masses of said fragmented peptides or proteins by mass-spectrometry to give the masses of one or more fragmented peptides or proteins selectively labeled with an isotope-distribution tag reagent; and
   (d) identifying a protein or peptide in a database using the mass of one and only one single fragmented peptide or protein selectively labeled with an isotope-distribution tag reagent and a sequence constraint derived from the specificity of the first isotope-distribution tag reagent and without determining the sequence of any ion derived from the one or more digested labeled peptides or proteins;
      wherein the mass of the single fragmented peptide or protein and the sequence constraint identifies a peptide or protein in the database.

* * * * *

UNITED STATES PATENT AND TRADEMARK OFFICE
CERTIFICATE OF CORRECTION

PATENT NO. : 6,629,040 B1
DATED : September 30, 2003
INVENTOR(S) : Goodlett et al.

It is certified that error appears in the above-identified patent and that said Letters Patent is hereby corrected as shown below:

<u>Column 6,</u>
Line 56, please replace "Tl" with -- Tl --.

<u>Column 7,</u>
Line 60, please replace "dimethylfornamide" with -- dimethylformamide --.

<u>Column 15,</u>
Line 32, please replace "every~3" with -- every ~3 --.

<u>Column 17,</u>
Line 11, please replace "within+\-1000" with -- within +\- 1000 --.

<u>Column 18,</u>
Line 39, please replace "56,352.60+/-191.73" with -- 56,352.60 +/- 191.73 --.

<u>Column 28,</u>
Line 41, please replace "in-the" with -- in the --.

<u>Column 31,</u>
Line 2, please replace "-determining" with -- determining --.
Line 8, please replace "or-more" with -- or more --.

Signed and Sealed this

Ninth Day of March, 2004

JON W. DUDAS
*Acting Director of the United States Patent and Trademark Office*

SEQUENCE LISTING

<160> NUMBER OF SEQ ID NOS: 22

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Test
      peptide

<400> SEQUENCE: 1

Arg Tyr Val Val Leu Pro Arg Pro Val Cys Phe Glu Lys
 1               5                  10

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Test
      peptide

<400> SEQUENCE: 2

Phe Leu Ala Ser Lys Leu Gly Asp Lys Ala Ala Ser Glu Leu Arg
 1               5                  10                  15

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Test
      peptide

<400> SEQUENCE: 3

Asp Lys Lys Arg Thr Arg Lys Asn Ala Glu Phe Gly Arg
 1               5                  10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Test
      peptide

```
<400> SEQUENCE: 4

Asn Leu Tyr Asp Ala Val Ser Asn Ile Thr Arg Leu Val Lys
  1               5                  10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Test
      peptide

<400> SEQUENCE: 5

Ile Glu Leu Phe Gln Arg Asn Lys Glu Ile Ser Thr Lys
  1               5                  10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Test
      peptide

<400> SEQUENCE: 6

Val Gln Leu Lys Ile Phe Glu Thr Asp Arg Gln Thr Lys
  1               5                  10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Test
      peptide

<400> SEQUENCE: 7

Glu Ser His Pro Val Gly Ile Leu Arg Asp Leu Ile Glu Lys
  1               5                  10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Test
      peptide

<400> SEQUENCE: 8

Glu Phe Asp Leu Leu Arg Ser Ile Ser Glu Lys Ile Arg
  1               5                  10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Test
      peptide

<400> SEQUENCE: 9

Ile Arg Thr Ala Glu Asp Glu Tyr Arg Ile Val Leu Lys
  1               5                  10

<210> SEQ ID NO 10
<211> LENGTH: 13
```

```
<212> TYPE: PRT
<213> ORGANISM: Artificial Sequence
<220> FEATURE:
<223> OTHER INFORMATION: Description of Artificial Sequence: Test
      peptide

<400> SEQUENCE: 10

Asp Lys Ile Glu Arg Ile Tyr Gly Leu Asn Lys Glu Lys
 1               5                  10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Test
      peptide

<400> SEQUENCE: 11

Tyr Leu Ala Lys Glu Glu Glu Lys Lys Gln Ala Leu Arg
 1               5                  10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Test
      peptide

<400> SEQUENCE: 12

Leu Asp Glu Phe Ile Lys Lys Asn Ser Asp Lys Ile Arg
 1               5                  10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Test
      peptide

<400> SEQUENCE: 13

Lys Ile Ser Ala Asp Leu Asn Lys Ile Asp Gly Leu Tyr Arg
 1               5                  10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Test
      peptide

<400> SEQUENCE: 14

Glu Lys Asn Gly Phe Asn Ile Glu Lys Lys Ala Leu Ser Lys
 1               5                  10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Test
      peptide

<400> SEQUENCE: 15

Asn Glu Ser Lys Ile Val Lys Arg Val Phe Glu Glu Lys
```

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Test peptide

<400> SEQUENCE: 16

Ile Lys Glu Leu Leu Phe Glu Leu Phe Tyr Tyr Lys
 1               5                  10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Test peptide

<400> SEQUENCE: 17

His Thr Val Thr Glu Leu Lys Ser Glu Ile His Ala Leu Lys
 1               5                  10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Test peptide

<400> SEQUENCE: 18

Glu Glu Val Lys Asp Ile Ile Glu Arg His Leu Pro Lys
 1               5                  10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Test peptide

<400> SEQUENCE: 19

Ala Lys Asp Lys Lys Lys Val Glu Asp Leu Phe Glu Arg
 1               5                  10

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Test peptide

<400> SEQUENCE: 20

Leu Thr Ser Ser Leu Ser Pro Ala Leu Pro Ala Gly Val His Gln Lys
 1               5                  10                  15

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Test -continued

```
        peptide

<400> SEQUENCE: 21

Arg Tyr Val Val Leu Pro Arg Pro Val Cys Phe Glu Lys Gly Met Asn
  1               5                  10                  15

Tyr Thr Val Arg
            20

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Test
        peptide

<400> SEQUENCE: 22

Gly Met Asn Tyr Thr Val Arg
  1               5
```